US 12,410,155 B2

(12) United States Patent
An et al.

(10) Patent No.: US 12,410,155 B2
(45) Date of Patent: *Sep. 9, 2025

(54) SALT FORM AND CRYSTAL FORM OF TETRAHYDROCYCLOHEPTA INDAZOLE COMPOUND

(71) Applicant: Zhejiang Yangli Pharmaceutical Technology Co., Ltd., Zhejiang (CN)

(72) Inventors: Ke An, Shanghai (CN); Shuhui Chen, Shanghai (CN)

(73) Assignee: ZHEJIANG YANGLI PHARMACEUTICAL TECHNOLOGY CO., LTD., Zhejiang (CN)

( * ) Notice: Subject to any disclaimer, the term of this patent is extended or adjusted under 35 U.S.C. 154(b) by 0 days.

This patent is subject to a terminal disclaimer.

(21) Appl. No.: 18/723,881

(22) PCT Filed: Dec. 28, 2022

(86) PCT No.: PCT/CN2022/142948
§ 371 (c)(1),
(2) Date: Aug. 14, 2024

(87) PCT Pub. No.: WO2023/125700
PCT Pub. Date: Jul. 6, 2023

(65) Prior Publication Data
US 2025/0084068 A1    Mar. 13, 2025

(30) Foreign Application Priority Data
Dec. 28, 2021 (CN) .......................... 202111631128.4

(51) Int. Cl.
*C07D 403/14* (2006.01)
(52) U.S. Cl.
CPC .................. *C07D 403/14* (2013.01)
(58) Field of Classification Search
CPC .................................................. C07D 403/14
See application file for complete search history.

(56) References Cited

U.S. PATENT DOCUMENTS

| | | | |
|---|---|---|---|
| 4,432,987 A * | 2/1984 | Barth .................. | A61P 31/04 514/193 |
| 6,518,288 B2 * | 2/2003 | Lemmens ............. | A61P 9/10 514/356 |
| 2016/0175289 A1 | 6/2016 | Labadie et al. | |
| 2017/0233340 A1 | 8/2017 | Bouaboula et al. | |
| 2018/0111931 A1 | 4/2018 | Barlaam et al. | |
| 2018/0170943 A1 | 6/2018 | Yu et al. | |
| 2023/0242507 A1 * | 8/2023 | An ..................... | C07D 401/14 |

FOREIGN PATENT DOCUMENTS

| | | |
|---|---|---|
| CN | 107108611 A | 8/2017 |
| CN | 108884079 A | 11/2018 |
| CN | 109843888 A | 6/2019 |
| WO | 2016202161 A1 | 12/2016 |
| WO | 2018077630 A1 | 5/2018 |
| WO | 2018091153 A1 | 5/2018 |
| WO | WO-2019002441 A1 * | 1/2019 |
| WO | 2019245974 A1 | 12/2019 |
| WO | 2020049150 A1 | 3/2020 |
| WO | 2022001971 A1 | 1/2022 |

OTHER PUBLICATIONS

S. Morissette, et al. Advanced Drug Delivery Reviews, vol. 56, Issue 3, 2004, pp. 275-300 (Year: 2004).*
S. Bharate, Journal of Drug Delivery Science and Technology, vol. 66, 2021, 102913, ISSN 1773-2247, https://doi.org/10.1016/j.jddst.2021.102913 (Year: 2021).*
International Search Report of PCT/CN2022/142948 issued on Mar. 2, 2023.
Written Opinion of International Search Authority of PCT/CN2022/142948 issued on Mar. 2, 2023.
Cheng, Y., Prusoff, W. H., Biochem. Pharmacol. 22:3099-3108, 1973.
RAD1901, Garner, F. et al., Anticancer Drugs, 2015, 26, 948-956.

* cited by examiner

*Primary Examiner* — James H Alstrum-Acevedo
*Assistant Examiner* — Manahil Mirghani Ali Abdalhameed
(74) *Attorney, Agent, or Firm* — Houston Beshining Law Office PLLC; Liangang Ye

(57) ABSTRACT

A class of salt forms and crystal forms of a tetrahydrocyclohepta indazole compound and a preparation method therefor. Specifically disclosed is the uses of the salt form and crystal form of the compound of formula (I) in the preparation of a drug for treating related diseases.

17 Claims, 12 Drawing Sheets

SALT FORM AND CRYSTAL FORM OF TETRAHYDROCYCLOHEPTA INDAZOLE COMPOUND

The present application is a National Stage of International Application No. PCT/CN2022/142948, filed on Dec. 28, 2022, which claims priority of the Chinese Patent Application No. CN202111631128.4 filed on Dec. 28, 2021, the contents of which are incorporated herein by reference in their entireties.

TECHNICAL FIELD

The present disclosure relates to a salt form and a crystal form of a tetrahydrocyclohepta indazole compound, and a preparation method therefor, and specifically relates to a use of the salt form and the crystal form of the compound of formula (I) in the preparation of a drug for treating related diseases.

BACKGROUND

According to WHO statistics, breast cancer has become the second most common cancer globally and the most common cancer among women. After years of research, the role of the estrogen-estrogen receptor signaling pathway in the development of breast cancer has been established, and the estrogen receptor (ER) has become the most important biomarker for breast cancer. Based on the expression of estrogen receptors, breast cancer can be classified into estrogen receptor-positive breast cancer and estrogen receptor-negative breast cancer; wherein, estrogen receptor-positive breast cancer accounts for more than 70% of all breast cancer cases.

Endocrine therapy (ET) targeting the estrogen-estrogen receptor signaling pathway in breast cancer cells has become the preferred treatment for estrogen receptor-positive breast cancer due to its minimal harm and significant efficacy. The first-line therapy for endocrine treatment is mainly aromatase inhibitors (AIs). Although the aromatase inhibitor Letrozole has shown good efficacy in treating estrogen receptor-positive breast cancer, the issue of resistance to aromatase inhibitors in estrogen receptor-positive breast cancer has become increasingly prominent with the application of these drugs. Extensive research indicates that estrogen receptors can undergo corresponding mutations in response to aromatase inhibitors, primarily the Y537X mutation. This mutation enables the mutated estrogen receptor to maintain an agonistic conformation in the absence of estrogen, allowing it to continue functioning as a receptor and promoting the proliferation of breast cancer cells. As the only marketed selective estrogen receptor degrader (SERD), fulvestrant has shown good efficacy in treating hormone therapy-resistant breast cancer. However, fulvestrant presents several issues in treating AI-resistant ER-mutant breast cancer. Firstly, due to its poor pharmacokinetic properties, fulvestrant exhibits near-zero oral bioavailability and has a high blood clearance rate. Consequently, this drug can only be administered via intramuscular injection. Moreover, due to its highly lipophilic structure, fulvestrant administered through intramuscular injection faces significant issues in tissue distribution. Clinically, only about 50% of breast cancer patients treated with fulvestrant show a clinical response. Additionally, due to its poor pharmacokinetic properties, the currently approved dose of fulvestrant does not achieve sufficient tissue concentrations to completely degrade ER, particularly mutant ER. Therefore, this treatment is not the optimal approach for AI-resistant ER-mutant breast cancer. Therefore, the development of drugs with better pharmacokinetic properties targeting ER-mutant breast cancer remains an unmet medical need.

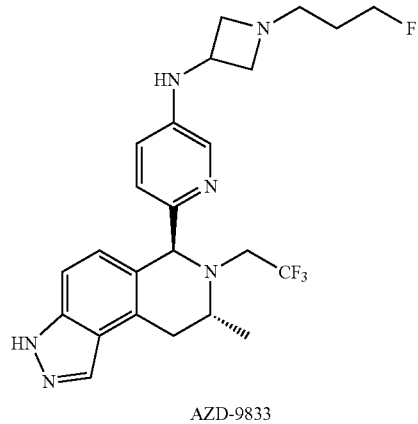 [SMILES: C[C@@H]1Cc2c(ccc3[nH]ncc23)[C@@H](c2ccc(NC3CN(CCCF)C3)cn2)N1CC(F)(F)F]

AZD-9833

The selective estrogen receptor degrader Elacestrant (RAD1901), developed by Radius and Menarini (Garner, F. et al., Anticancer Drugs, 2015, 26, 948-956), demonstrated superior progression-free survival compared to standard therapies in Phase III clinical trials, particularly benefiting patients with ESR1 mutations. An NDA has been submitted to the FDA. WO2018/077630A1 reports that AstraZeneca is currently developing a new generation non-covalent estrogen receptor degrader, Camizestrant (AZD9833), for the treatment of ER-positive breast cancer. This molecule is currently undergoing a Phase III clinical trial for the treatment of ER-positive, HER2-negative breast cancer. WO2019/245974A1 and WO2020/049150A1 respectively report that Genentech and Sanofi are developing new generation non-covalent estrogen receptor degraders, Giredestrant (GDC-9545) and Amcenestrant (SAR439859). Giredestrant is in Phase III clinical trials, but its monotherapy in Phase II trials did not show an advantage over existing therapies. Amcenestrant did not demonstrate an advantage in Phase II trials and its development has been discontinued.

Content of the Present Invention

The present disclosure provides a compound of formula (III)

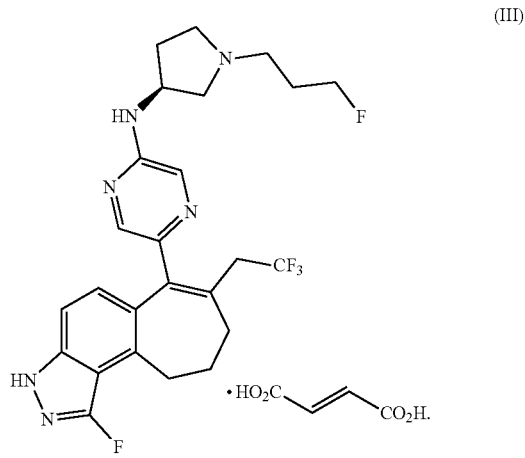 [SMILES: FCCCN1CC[C@H](Nc2cnc(C3=C(CC(F)(F)F)CCCc4c3ccc3[nH]nc(F)c43)cn2)C1 ; O=C(O)/C=C/C(=O)O]

The present disclosure further provides a crystal form A of the compound of formula (III),

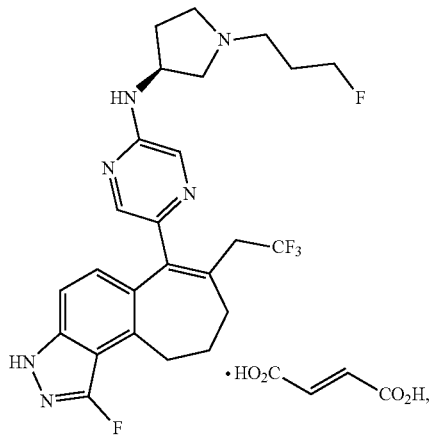

(III)

wherein the crystal form A has an X-ray powder diffraction pattern comprising characteristic diffraction peaks at the following 2θ angles: 20.92±0.20°, 22.08±0.20°, and 24.70±0.20°.

In some embodiments of the present disclosure, the crystal form A of the compound of formula (III) is provided, wherein the X-ray powder diffraction pattern thereof comprises diffraction peaks at the following 2θ angles: 12.30±0.20°, 15.64±0.20°, 17.00±0.20°, 18.26±0.20°, 20.92±0.20°, 22.08±0.20°, 22.62±0.20°, and 24.70±0.20°.

In some embodiments of the present disclosure, the crystal form A of the compound of formula (III) is provided, wherein the X-ray powder diffraction pattern thereof comprises diffraction peaks at the following 2θ angles: 5.18±0.20°, 5.92±0.20°, 8.12±0.20°, 12.30±0.20°, 15.64±0.20°, 17.00±0.20°, 18.26±0.20°, 20.92±0.20°, 22.08±0.20°, and 24.70±0.20°.

In some embodiments of the present disclosure, the crystal form A of the compound of formula (III) is provided, wherein the X-ray powder diffraction pattern thereof comprises diffraction peaks at the following 2θ angles: 5.18±0.20°, 5.92±0.20°, 8.12±0.20°, 12.30±0.20°, 15.64±0.20°, 17.00±0.20°, 18.26±0.20°, 19.54±0.20°, 20.92±0.20°, 22.08±0.20°, 22.62±0.20°, and 24.70±0.20°.

In some embodiments of the present disclosure, the crystal form A of the compound of formula (III) is provided, wherein the X-ray powder diffraction pattern thereof comprises diffraction peaks at the following 2θ angles: 5.18±0.20°, 5.92±0.20°, 8.12±0.20°, 12.30±0.20°, 15.64±0.20°, 17.00±0.20°, 18.26±0.20°, 19.54±0.20°, 20.92±0.20°, 22.08±0.20°, 24.70±0.20°, and 25.48±0.20°.

In some embodiments of the present disclosure, the crystal form A of the compound of formula (III) is provided, wherein the X-ray powder diffraction pattern thereof comprises diffraction peaks at the following 2θ angles: 5.18±0.20°, 5.92±0.20°, 8.12±0.20°, 12.30±0.20°, 15.64±0.20°, 17.00±0.20°, 18.26±0.20°, 19.54±0.20°, 20.92±0.20°, 22.08±0.20°, 22.62±0.20°, 24.70±0.20°, and 25.48±0.20°.

In some embodiments of the present disclosure, the crystal form A of the compound of formula (III) is provided, wherein the X-ray powder diffraction pattern thereof comprises diffraction peaks at the following 2θ angles: 5.18±0.20°, 5.92±0.20°, 8.12±0.20°, 12.30±0.20°, 15.64±0.20°, 16.42±0.20°, 17.00±0.20°, 17.66±0.20°, 18.26±0.20°, 19.54±0.20°, 20.06±0.20°, 20.92±0.20°, 22.08±0.20°, 22.62±0.20°, 23.32±0.20°, 23.86±0.20°, 24.70±0.20°, 25.48±0.20°, 26.68±0.20°, 28.50±0.20°, 29.54±0.20°, 31.58±0.20°, and 33.20±0.20°.

In some embodiments of the present disclosure, the crystal form A of the compound of formula (III) is provided, wherein the X-ray powder diffraction pattern thereof comprises diffraction peaks at the following 2θ angles: 5.181°, 5.920°, 8.119°, 12.299°, 15.638°, 16.418°, 17.002°, 17.660°, 18.261°, 19.539°, 20.061°, 20.919°, 22.080°, 22.621°, 23.320°, 23.861°, 24.700°, 25.483°, 26.681°, 28.498°, 29.542°, 31.578°, and 33.198°.

In some embodiments of the present disclosure, the crystal form A of the compound of formula (III) is provided, wherein the X-ray powder diffraction pattern thereof is basically as shown in FIG. 1.

In some embodiments of the present disclosure, the analysis data of the XRPD pattern of the crystal form A are as shown in Table 1:

TABLE 1

Analysis data of XRPD pattern of crystal form A of compound of formula (III)

| No. | 2θ angle (°) | d-Spacing (Å) | Intensity (counts) | Relative intensity (%) |
|---|---|---|---|---|
| 1 | 5.181 | 17.0414 | 90 | 17.60 |
| 2 | 5.920 | 14.9174 | 102 | 20.00 |
| 3 | 8.119 | 10.8806 | 68 | 13.20 |
| 4 | 12.299 | 7.1909 | 360 | 70.30 |
| 5 | 15.638 | 5.6621 | 444 | 86.80 |
| 6 | 16.418 | 5.3948 | 327 | 64.00 |
| 7 | 17.002 | 5.2109 | 337 | 65.90 |
| 8 | 17.660 | 5.0180 | 314 | 61.40 |
| 9 | 18.261 | 4.8543 | 416 | 81.40 |
| 10 | 19.539 | 4.5396 | 276 | 54.00 |
| 11 | 20.061 | 4.4227 | 209 | 40.90 |
| 12 | 20.919 | 4.2431 | 458 | 89.60 |
| 13 | 22.080 | 4.0225 | 454 | 88.80 |
| 14 | 22.621 | 3.9276 | 361 | 70.60 |
| 15 | 23.320 | 3.8114 | 334 | 65.30 |
| 16 | 23.861 | 3.7262 | 336 | 65.70 |
| 17 | 24.700 | 3.6014 | 512 | 100.00 |
| 18 | 25.483 | 3.4926 | 262 | 51.20 |
| 19 | 26.681 | 3.3384 | 85 | 16.70 |
| 20 | 28.498 | 3.1296 | 90 | 17.60 |
| 21 | 29.542 | 3.0212 | 61 | 11.90 |
| 22 | 31.578 | 2.8310 | 75 | 14.70 |
| 23 | 33.198 | 2.6964 | 64 | 12.50 |

In some embodiments of the present disclosure, the crystal form A of the compound of formula (III) is provided, wherein the X-ray powder diffraction pattern thereof comprises diffraction peaks at the following 2θ angles; and/or 5.18±0.20°, and/or 5.92±0.20°, and/or 8.12±0.20°, and/or 12.30±0.20°, and/or 15.64±0.20°, and/or 16.42±0.20°, and/or 17.00±0.20°, and/or 17.66±0.20°, and/or 18.26±0.20°, and/or 19.54±0.20°, and/or 20.06±0.20°, and/or 20.92±0.20°, and/or 22.08±0.20°, and/or 22.62±0.20°, and/or 23.32±0.20°, and/or 23.86±0.20°, and/or 24.70±0.20°, and/or 25.48±0.20°, and/or 26.68±0.20°, and/or 28.50±0.20°, and/or 29.54±0.20°, and/or 31.58±0.20°, and/or 33.20±0.20°.

In some embodiments of the present disclosure, the crystal form A of the compound of formula (III) is provided, wherein the crystal form A has a thermogravimetric analysis curve with a weight loss of 0.198% at 150.000±3° C. and a weight loss of 10.880% at 240.000±3° C.

In some embodiments of the present disclosure, the crystal form A of the compound of formula (III) is provided, wherein the thermogravimetric analysis curve thereof is as shown in FIG. 2.

In some embodiments of the present disclosure, the crystal form A of the compound of formula (III) is provided, wherein the crystal form A has a differential scanning calorimetry curve comprising endothermic peaks with onsets at 175.87±5° C., 214.68±5° C., and 292.11±5° C.

In some embodiments of the present disclosure, the crystal form A of the compound of formula (III) is provided, wherein the differential scanning calorimetry curve thereof is as shown in FIG. 3.

The present disclosure further provides a crystal form B of a compound of formula (II),

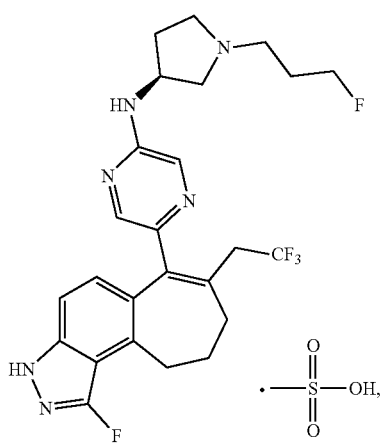

(II)

wherein the crystal form B has an X-ray powder diffraction pattern comprising characteristic diffraction peaks at the following 2θ angles: 14.24±0.20°, 22.18±0.20°, and 23.78±0.20°.

In some embodiments of the present disclosure, the crystal form B of the compound of formula (II) is provided, wherein the X-ray powder diffraction pattern thereof comprises diffraction peaks at the following 2θ angles: 6.50±0.20°, 14.24±0.20°, 15.80±0.20°, 18.18±0.20°, 22.18±0.20°, 23.78±0.20°, and 25.30±0.20°.

In some embodiments of the present disclosure, the crystal form B of the compound of formula (II) is provided, wherein the X-ray powder diffraction pattern thereof comprises diffraction peaks at the following 2θ angles: 6.50±0.20°, 7.86±0.20°, 14.24±0.20°, 15.80±0.20°, 16.92±0.20°, 18.18±0.20°, 19.66±0.20°, 20.76±0.20°, 22.18±0.20°, 23.78±0.20°, 25.30±0.20°, and 26.12±0.20°.

In some embodiments of the present disclosure, the crystal form B of the compound of formula (II) is provided, wherein the X-ray powder diffraction pattern thereof comprises diffraction peaks at the following 2θ angles: 6.499°, 7.860°, 9.739°, 10.257°, 11.862°, 12.255°, 13.021°, 14.240°, 15.417°, 15.797°, 16.541°, 16.920°, 17.558°, 18.182°, 18.439°, 18.702°, 19.660°, 20.381°, 20.761°, 21.494°, 21.647°, 22.180°, 23.781°, 24.099°, 24.498°, 25.304°, 26.118°, 26.821°, 27.239°, 28.579°, 28.924°, 29.302°, 29.881°, 30.278°, 30.681°, 30.938°, 31.764°, 32.978°, 34.260°, 35.101°, 35.419°, 35.761°, 36.597°, 37.083°, 37.540°, and 38.423°.

In some embodiments of the present disclosure, the analysis data of the XRPD pattern of the crystal form B are as shown in Table 2:

TABLE 2

Analysis data of XRPD pattern of crystal form B of compound of formula (II)

| No. | 2θ angle (°) | d-Spacing (Å) | Intensity (counts) | Relative intensity (%) |
|---|---|---|---|---|
| 1 | 6.499 | 13.5887 | 519 | 49.70 |
| 2 | 7.860 | 11.2387 | 357 | 34.20 |
| 3 | 9.739 | 9.0749 | 59 | 5.60 |
| 4 | 10.257 | 8.6170 | 151 | 14.50 |
| 5 | 11.862 | 7.4549 | 76 | 7.30 |
| 6 | 12.255 | 7.2164 | 138 | 13.20 |
| 7 | 13.021 | 6.7937 | 219 | 20.90 |
| 8 | 14.240 | 6.2146 | 930 | 89.00 |
| 9 | 15.417 | 5.7427 | 103 | 9.90 |
| 10 | 15.797 | 5.6054 | 489 | 46.80 |
| 11 | 16.541 | 5.3550 | 168 | 16.10 |
| 12 | 16.920 | 5.2358 | 270 | 25.80 |
| 13 | 17.558 | 5.0470 | 60 | 5.70 |
| 14 | 18.182 | 4.8751 | 544 | 52.00 |
| 15 | 18.439 | 4.8078 | 164 | 15.70 |
| 16 | 18.702 | 4.7407 | 175 | 16.80 |
| 17 | 19.660 | 4.5119 | 348 | 33.30 |
| 18 | 20.381 | 4.3539 | 269 | 25.80 |
| 19 | 20.761 | 4.2750 | 301 | 28.80 |
| 20 | 21.494 | 4.1308 | 64 | 6.10 |
| 21 | 21.647 | 4.1020 | 69 | 6.60 |
| 22 | 22.180 | 4.0047 | 1045 | 100.00 |
| 23 | 23.781 | 3.7385 | 868 | 83.00 |
| 24 | 24.099 | 3.6899 | 858 | 82.10 |
| 25 | 24.498 | 3.6308 | 220 | 21.10 |
| 26 | 25.304 | 3.5169 | 621 | 59.40 |
| 27 | 26.118 | 3.4090 | 319 | 30.50 |
| 28 | 26.821 | 3.3213 | 116 | 11.10 |
| 29 | 27.239 | 3.2713 | 84 | 8.10 |
| 30 | 28.579 | 3.1208 | 71 | 6.80 |
| 31 | 28.924 | 3.0844 | 66 | 6.30 |
| 32 | 29.302 | 3.0455 | 45 | 4.30 |
| 33 | 29.881 | 2.9878 | 87 | 8.40 |
| 34 | 30.278 | 2.9495 | 100 | 9.60 |
| 35 | 30.681 | 2.9117 | 42 | 4.10 |
| 36 | 30.938 | 2.8880 | 62 | 5.90 |
| 37 | 31.764 | 2.8148 | 75 | 7.20 |
| 38 | 32.978 | 2.7139 | 75 | 7.20 |
| 39 | 34.260 | 2.6152 | 53 | 5.10 |
| 40 | 35.101 | 2.5545 | 110 | 10.60 |
| 41 | 35.419 | 2.5323 | 88 | 8.40 |
| 42 | 35.761 | 2.5089 | 105 | 10.00 |
| 43 | 36.597 | 2.4534 | 28 | 2.70 |
| 44 | 37.083 | 2.4224 | 41 | 3.90 |
| 45 | 37.540 | 2.3939 | 38 | 3.70 |
| 46 | 38.423 | 2.3409 | 35 | 3.30 |

In some embodiments of the present disclosure, the crystal form B of the compound of formula (II) is provided, wherein the X-ray powder diffraction pattern thereof comprises diffraction peaks at the following 2θ angles; and/or 6.50±0.20°, and/or 7.86±0.20°, and/or 9.74±0.20°, and/or 10.26±0.20°, and/or 11.86±0.20°, and/or 12.26±0.20°, and/or 13.02±0.20°, and/or 14.24±0.20°, and/or 15.42±0.20°, and/or 15.80±0.20°, and/or 16.54±0.20°, and/or 16.92±0.20°, and/or 17.56±0.20°, and/or 18.18±0.20°, and/or 18.44±0.20°, and/or 18.70±0.20°, and/or 19.66±0.20°, and/or 20.38±0.20°, and/or 20.76±0.20°, and/or 21.49±0.20°, and/or 21.65±0.20°, and/or 22.18±0.20°, and/or 23.78±0.20°, and/or 24.10±0.20°, and/or 24.50±0.20°, and/or 25.30±0.20°, and/or 26.12±0.20°, and/or 26.82±0.20°, and/or 27.24±0.20°, and/or 28.58±0.20°, and/or 28.92±0.20°, and/or 29.30±0.20°, and/or 29.88±0.20°, and/or 30.28±0.20°, and/or 30.68±0.20°, and/or 30.94±0.20°, and/or 31.76±0.20°, and/or 32.98±0.20°, and/or 34.26±0.20°, and/or 35.10±0.20°, and/or 35.42±0.20°, and/or 35.76±0.20°, and/or 36.60±0.20°, and/or 37.08±0.20°, and/or 37.54±0.20°, and/or 38.42±0.20°.

In some embodiments of the present disclosure, the crystal form B of the compound of formula (II) is provided, wherein the X-ray powder diffraction pattern thereof is basically as shown in FIG. 4.

In some embodiments of the present disclosure, the crystal form B of the compound of formula (II) is provided, wherein the crystal form B has a thermogravimetric analysis curve with a weight loss of 0.085% at 200.000±3° C.

In some embodiments of the present disclosure, the crystal form B of the compound of formula (II) is provided, wherein the thermogravimetric analysis curve thereof is as shown in FIG. 5.

In some embodiments of the present disclosure, the crystal form B of the compound of formula (II) is provided, wherein the crystal form B has a differential scanning calorimetry curve comprising an endothermic peak with an onset at 215.60±3° C.

In some embodiments of the present disclosure, the crystal form B of the compound of formula (II) is provided, wherein the differential scanning calorimetry curve thereof is as shown in FIG. 6.

The present disclosure further provides a crystal form C of a compound of formula (I),

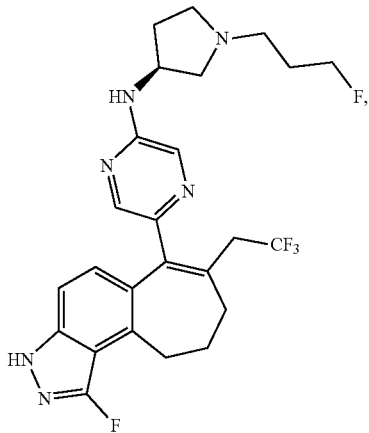

(I)

wherein the crystal form C has an X-ray powder diffraction pattern comprising characteristic diffraction peaks at the following 2θ angles: 4.90±0.20°, 15.82±0.20°, and 22.26±0.20°.

In some embodiments of the present disclosure, the crystal form C of the compound of formula (I) is provided, wherein the X-ray powder diffraction pattern thereof comprises diffraction peaks at the following 2θ angles: 4.90±0.20°, 9.82±0.20°, 15.82±0.20°, 17.48±0.20°, 18.64±0.20°, 22.26±0.20°, 23.74±0.20°, and 29.36±0.20°.

In some embodiments of the present disclosure, the crystal form C of the compound of formula (I) is provided, wherein the X-ray powder diffraction pattern thereof comprises diffraction peaks at the following 2θ angles: 3θ±0.20°, 4.90±0.20°, 9.82±0.20°, 11.06±0.20°, 14.20±0.20°, 15.82±0.20°, 17.48±0.20°, 18.64±0.20°, 22.26±0.20°, 23.74±0.20°, 24.46±0.20°, and 29.36±0.20°.

In some embodiments of the present disclosure, the crystal form C of the compound of formula (I) is provided, wherein the X-ray powder diffraction pattern thereof comprises diffraction peaks at the following 2θ angles: 3.301°, 4.901°, 7.898°, 9.319°, 9.819°, 11.061°, 14.200°, 14.721°, 15.197°, 15.821°, 16.457°, 17.481°, 18.101°, 18.642°, 19.762°, 20.961°, 21.382°, 22.259°, 23.740°, 24.461°, 25.761°, 26.295°, 26.943°, 27.518°, 29.358°, 30.075°, 31.317°, 31.916°, 34.598°, and 37.661°.

In some embodiments of the present disclosure, the analysis data of the XRPD pattern of the crystal form C are as shown in Table 3:

TABLE 3

Analysis data of XRPD pattern of crystal form C of compound of formula (I)

| No. | 2θ angle (°) | d-Spacing (Å) | Intensity (counts) | Relative intensity (%) |
|---|---|---|---|---|
| 1 | 3.301 | 26.7429 | 205 | 25.70 |
| 2 | 4.901 | 18.0175 | 577 | 72.30 |
| 3 | 7.898 | 11.1855 | 45 | 5.70 |
| 4 | 9.319 | 9.4821 | 41 | 5.20 |
| 5 | 9.819 | 9.0004 | 348 | 43.60 |
| 6 | 11.061 | 7.9929 | 197 | 24.70 |
| 7 | 14.200 | 6.2319 | 221 | 27.70 |
| 8 | 14.721 | 6.0127 | 35 | 4.30 |
| 9 | 15.197 | 5.8253 | 102 | 12.70 |
| 10 | 15.821 | 5.5971 | 460 | 57.70 |
| 11 | 16.457 | 5.3820 | 49 | 6.20 |
| 12 | 17.481 | 5.0691 | 281 | 35.20 |
| 13 | 18.101 | 4.8969 | 223 | 27.90 |
| 14 | 18.642 | 4.7558 | 310 | 38.90 |
| 15 | 19.762 | 4.4889 | 162 | 20.40 |
| 16 | 20.961 | 4.2347 | 106 | 13.30 |
| 17 | 21.382 | 4.1523 | 124 | 15.50 |
| 18 | 22.259 | 3.9906 | 798 | 100.00 |
| 19 | 23.740 | 3.7449 | 324 | 40.60 |
| 20 | 24.461 | 3.6361 | 208 | 26.10 |
| 21 | 25.761 | 3.4555 | 72 | 9.00 |
| 22 | 26.295 | 3.3866 | 89 | 11.10 |
| 23 | 26.943 | 3.3066 | 158 | 19.80 |
| 24 | 27.518 | 3.2388 | 57 | 7.20 |
| 25 | 29.358 | 3.0398 | 300 | 37.60 |
| 26 | 30.075 | 2.9690 | 46 | 5.70 |
| 27 | 31.317 | 2.8540 | 56 | 7.00 |
| 28 | 31.916 | 2.8018 | 83 | 10.40 |
| 29 | 34.598 | 2.5904 | 49 | 6.10 |
| 30 | 37.661 | 2.3865 | 48 | 6.00 |

In some embodiments of the present disclosure, the crystal form C of the compound of formula (I) is provided, wherein the X-ray powder diffraction pattern thereof comprises diffraction peaks at the following 2θ angles; and/or 3.30±0.20°, and/or 4.90±0.20°, and/or 7.90±0.20°, and/or 9.32±0.20°, and/or 9.82±0.20°, and/or 11.06±0.20°, and/or 14.20±0.20°, and/or 14.72±0.20°, and/or 15.20±0.20°, and/or 15.82±0.20°, and/or 16.46±0.20°, and/or 17.48±0.20°, and/or 18.10±0.20°, and/or 18.64±0.20°, and/or 19.76±0.20°, and/or 20.96±0.20°, and/or 21.38±0.20°, and/or 22.26±0.20°, and/or 23.74±0.20°, and/or 24.46±0.20°, and/or 25.76±0.20°, and/or 26.30±0.20°, and/or 26.94±0.20°, and/or 27.52±0.20°, and/or 29.36±0.20°, and/or 30.08±0.20°, and/or 31.32±0.20°, and/or 31.92±0.20°, and/or 34.60±0.20°, and/or 37.66±0.20°.

In some embodiments of the present disclosure, the crystal form C of the compound of formula (I) is provided, wherein the X-ray powder diffraction pattern thereof is basically as shown in FIG. 7.

In some embodiments of the present disclosure, the crystal form C of the compound of formula (I) is provided, wherein the crystal form C has a differential scanning calorimetry curve comprising an endothermic peak with an onset at 124.14±5° C., and exothermic peaks with onsets at 199.34±5° C. and 278.70±5° C.

In some embodiments of the present disclosure, the crystal form C of the compound of formula (I) is provided, wherein the differential scanning calorimetry curve thereof is as shown in FIG. 8.

The present disclosure further provides a crystal form of the compound of formula (II), wherein its crystal structure is as shown in FIG. 9.

The present disclosure further provides a use of the compounds and the crystal forms thereof in the manufacture of a medicament for treating ESR1-positive tumors.

Technical Effect

The compounds of the present disclosure exhibit good pharmacokinetic properties and oral absorption rates, with stable crystal forms.

The compounds of the present disclosure demonstrate excellent activity against both wild-type and mutant ESR1-positive tumor models and show superior efficacy in various ESR1-positive cell types. These compounds may provide more effective treatment options for patients with ER+/HER2− locally advanced or metastatic breast cancer.

Definition and Description

The following abbreviations are used in the present disclosure: DMSO represents dimethyl sulfoxide; TsOH represents p-toluenesulfonic acid; PBS represents 0.9% sodium chloride phosphate-buffer solution; THP represents tetrahydropyranyl; Nf represents perfluoro-1-butyl.

The term "Weight loss" refers to weight lost; "Weight percent loss" refers to the percentage of weight lost; "Residue" refers to the remaining substance; "Residue percent" indicates the percentage of the remaining substance; "Integral" refers to the total amount of exothermic (or endothermic) energy; "Normalized" refers to the standardized measurement of exothermic (or endothermic) energy; "Peak" refers to the peak value; "Onset" refers to the initial melting temperature; "Endset" refers to the final melting temperature; "Left limit" refers to the left boundary temperature, and "Right limit" refers to the right boundary temperature.

The compounds of the present disclosure are named according to the conventional naming principles in the art or by ChemDraw® software, and the commercially available compounds are named according to the supplier catalog names.

X-Ray Powder Diffraction (X-Ray Powder Diffractometer, XRPD) Method of the Present Disclosure Instrument model: Bruker D8 advance X-ray diffractometer Test method: Approximately 10 to 20 mg of sample is used for XRPD detection.

The detailed XRPD parameters are as follows:
Light tube: Cu, kα, (λ=1.54056 Å).
Light tube voltage: 40 kV, light tube current: 40 mA
Divergence slit: 0.60 mm
Detector slit: 10.50 mm
Anti-scatter slit: 7.10 mm
Scan range: 4 to 40 deg
Step size: 0.02 deg
Step time: 0.12 seconds
Sample plate rotation speed: 15 rpm Differential Scanning Calorimetry (Differential Scanning Calorimeter, DSC) Method of the Present Disclosure Instrument model: TA Q2000 differential scanning calorimeter Testing method: Approximately 1 mg of the sample is placed in a DSC aluminum pan for testing. Under 50 mL/min of nitrogen, the sample is heated from 30° C. (room temperature) to 300° C. (or 350° C.) at a heating rate of 10° C./min.

Thermogravimetric Analysis (Thermal Gravimetric Analyzer, TGA) Method of the Present Disclosure Instrument model: TA Q5000IR thermal gravimetric analyzer Testing method: Approximately 2 to 5 mg of the sample is placed in a TGA platinum pan for testing. Under 25 mL/min of nitrogen, the sample is heated from room temperature to 350° C. or until a 20% weight loss, at a heating rate of 10° C./min.

Single Crystal Diffraction Method of the Present Disclosure

Sample culture: 2 mg of the compound of formula (II) is dissolved in 400 μL of methanol/ethyl acetate (1:1) at room temperature. The sample solution is placed in a 1 mL semi-sealed vial and allowed to evaporate slowly at room temperature. Crystals are obtained the next day, and the crystal structures are as shown in FIG. 9.

Instrument model: Rigaku Oxford Diffraction XtaLAB Synergy-S four-circle diffractometer equipped with a HyPix-6000HE area detector.

DETAILED DESCRIPTION OF THE PREFERRED EMBODIMENT

Figure 1:
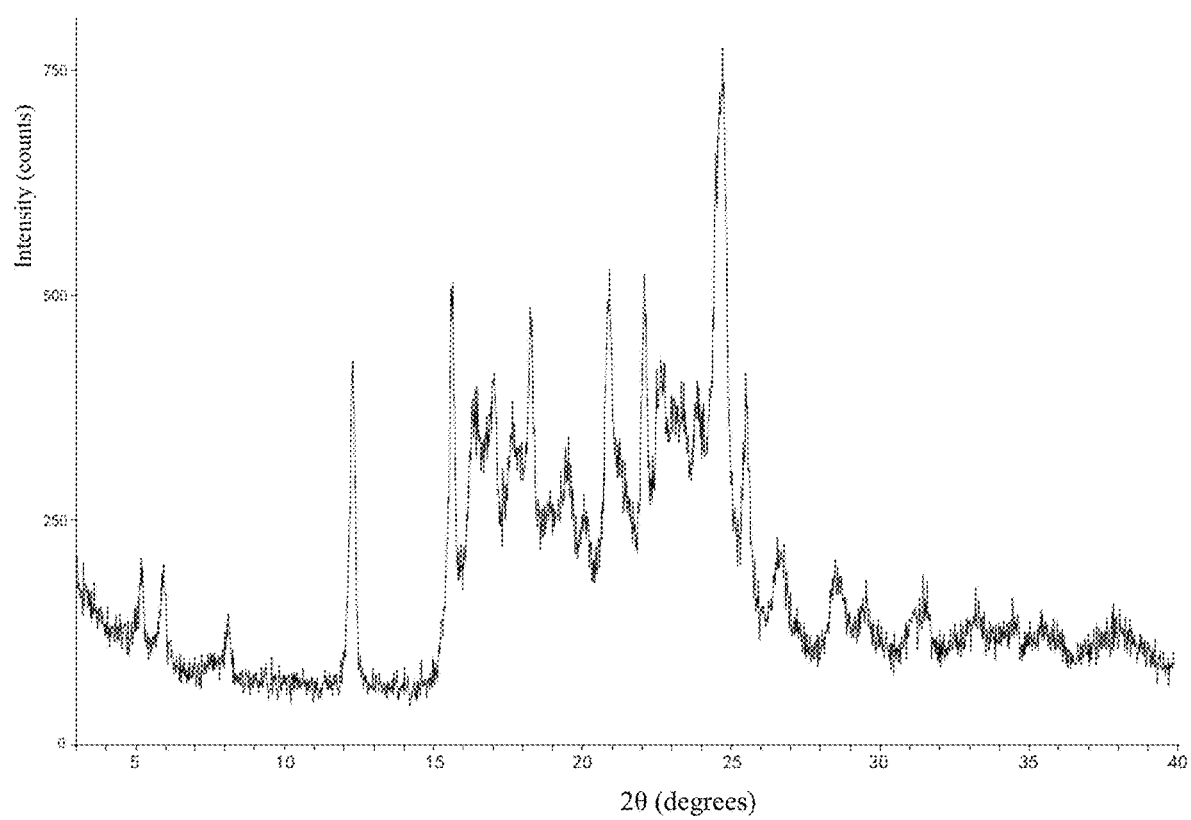
FIG. 1 shows a XRPD pattern of the crystal form A of the compound of formula (III).
Figure 2:
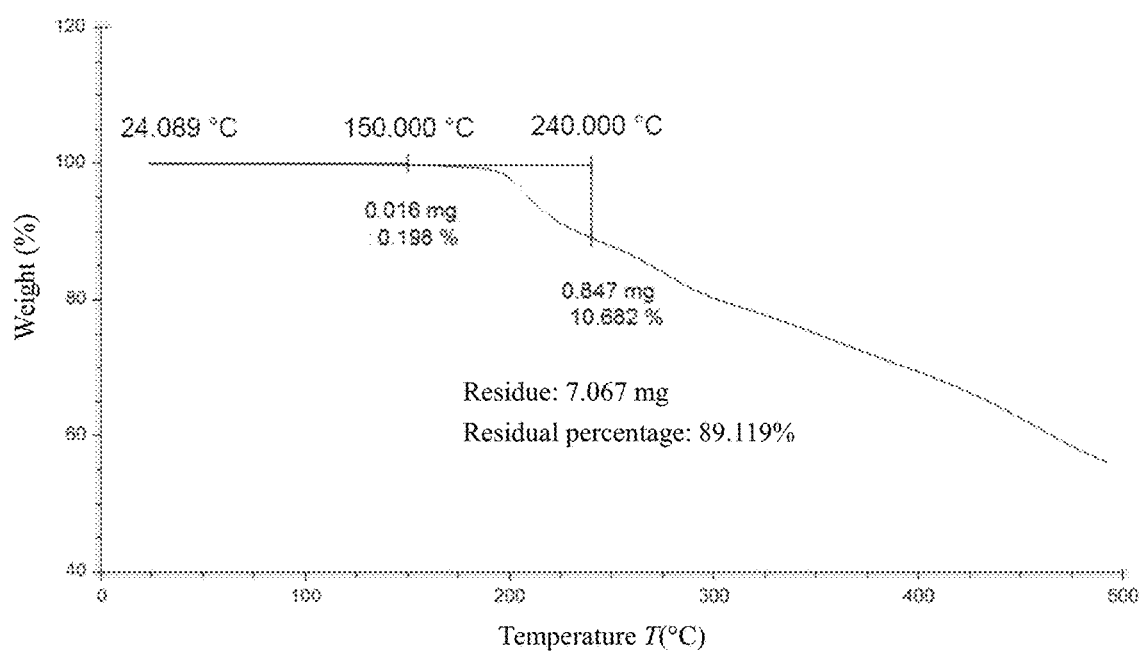
FIG. 2 shows a TGA pattern of the crystal form A of the compound of formula (III).
Figure 3:
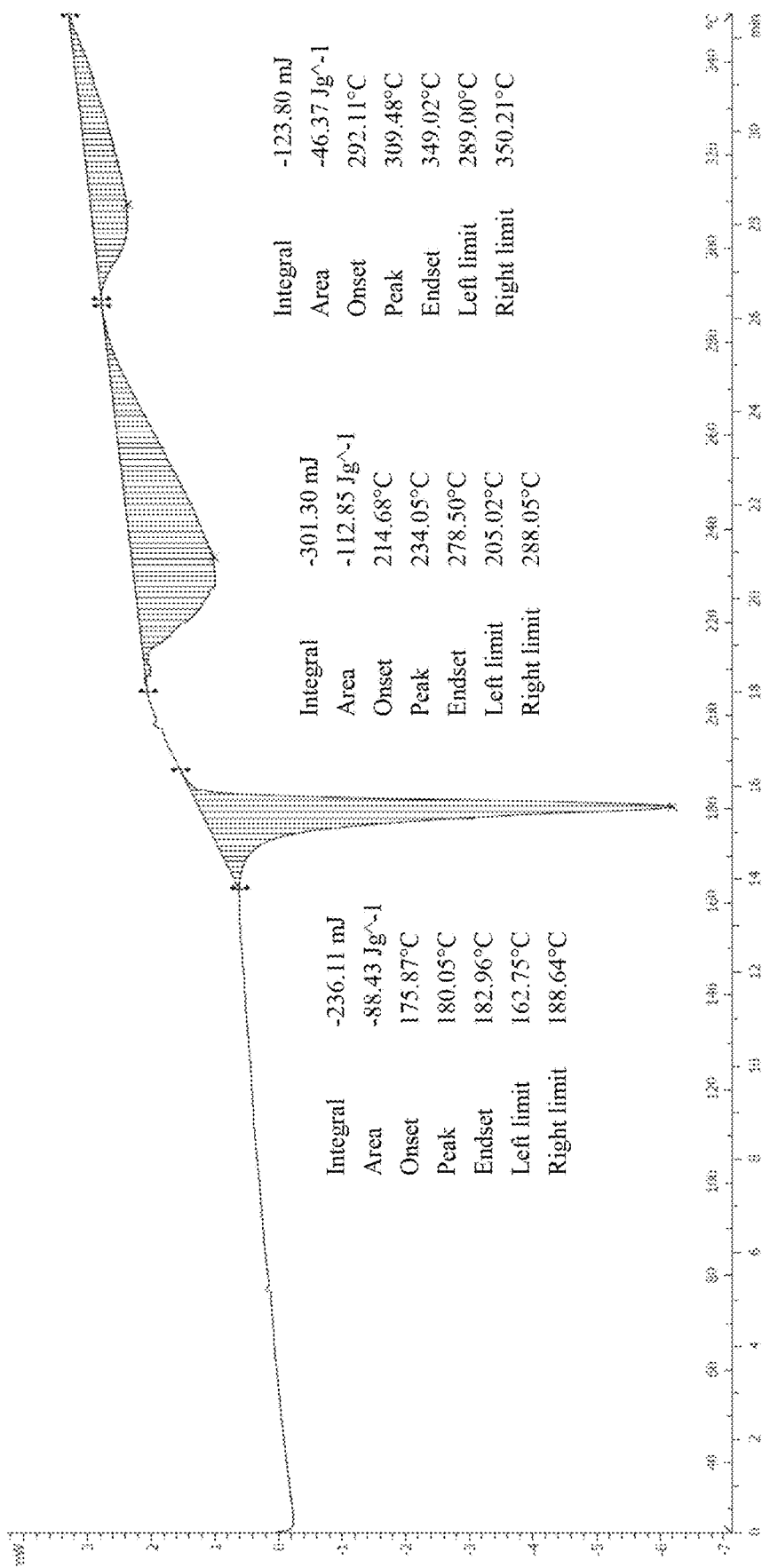
FIG. 3 shows a DSC pattern of the crystal form A of the compound of formula (III).
Figure 4:
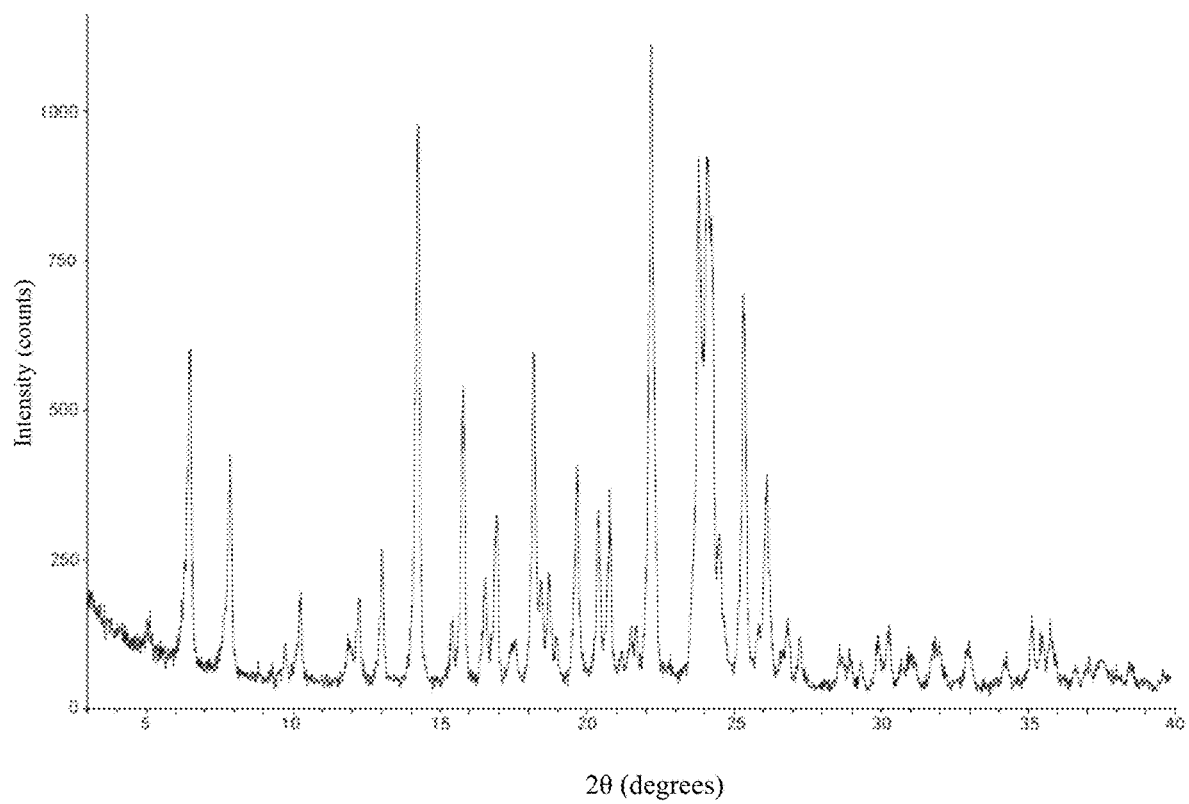
FIG. 4 shows a XRPD pattern of the crystal form B of the compound of formula (II).
Figure 5:
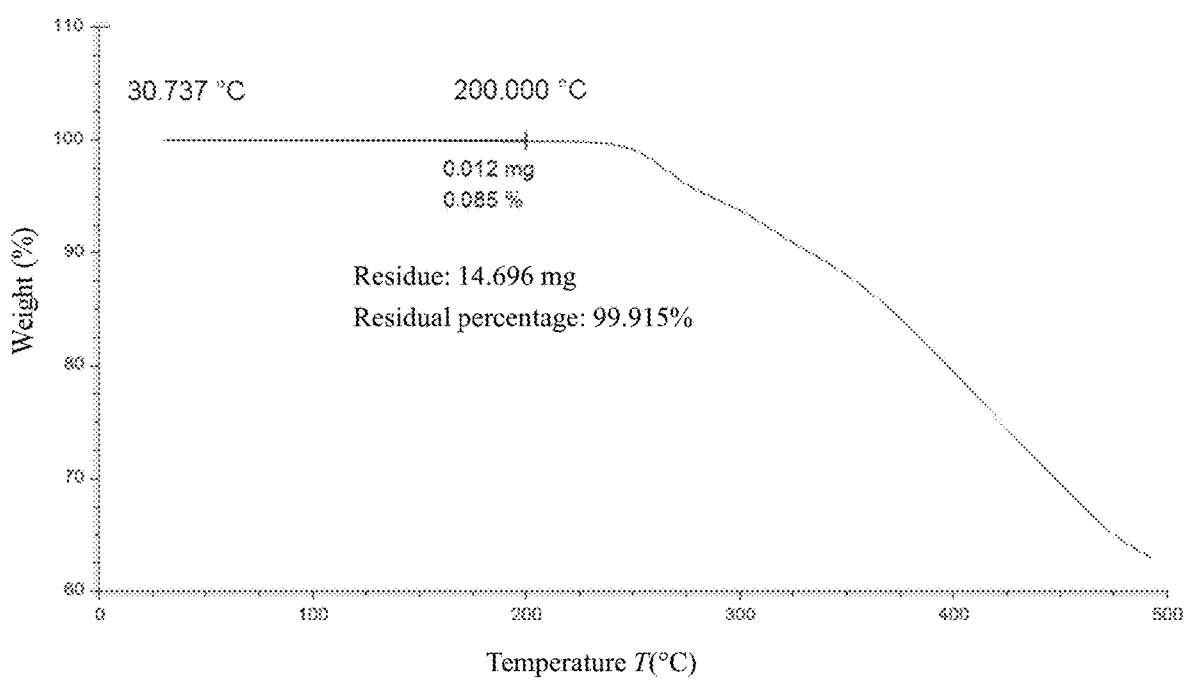
FIG. 5 shows a TGA pattern of the crystal form B of the compound of formula (II).
Figure 6:
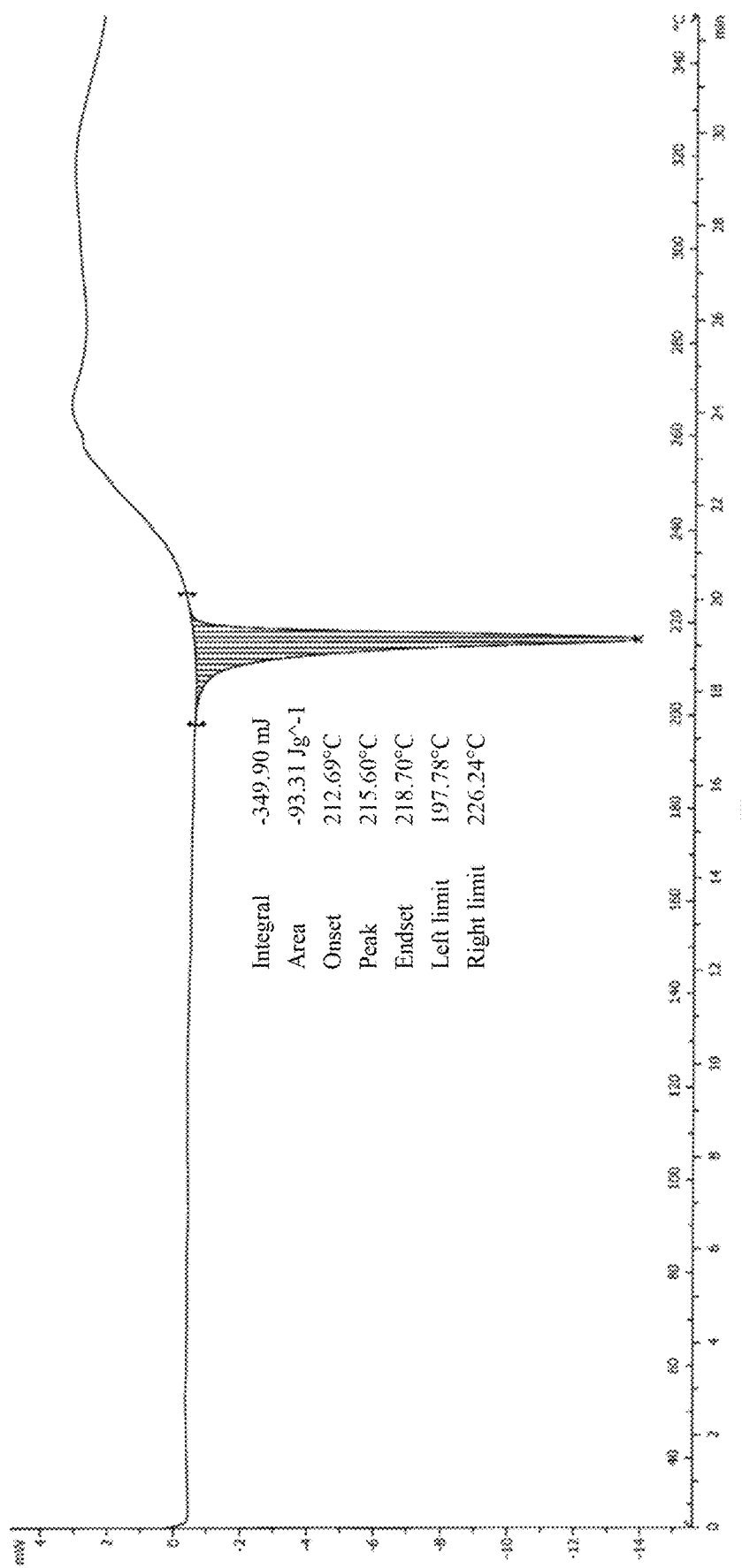
FIG. 6 shows a DSC pattern of the crystal form B of the compound of formula (II).
Figure 7:
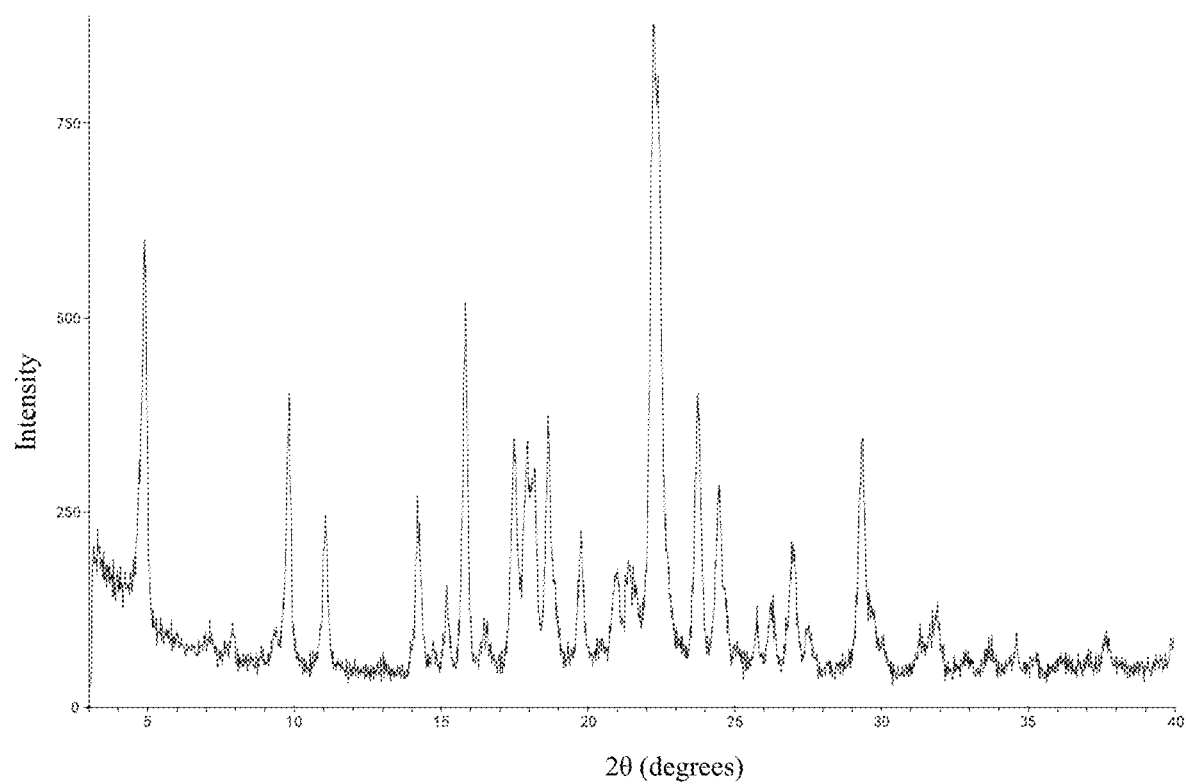
FIG. 7 shows a XRPD pattern of the crystal form C of the compound of formula (I).
Figure 8:
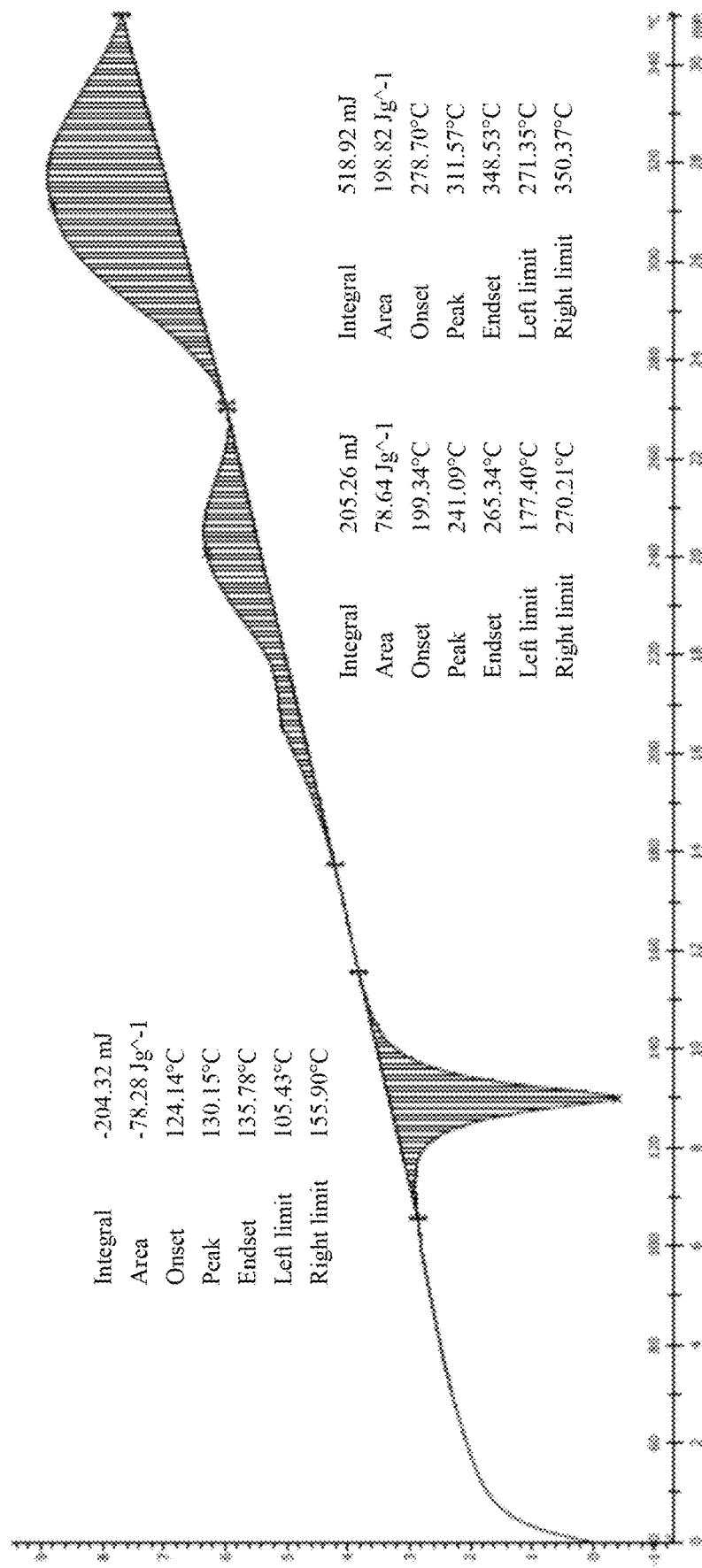
FIG. 8 shows a DSC pattern of the crystal form C of the compound of formula (I).
Figure 9:
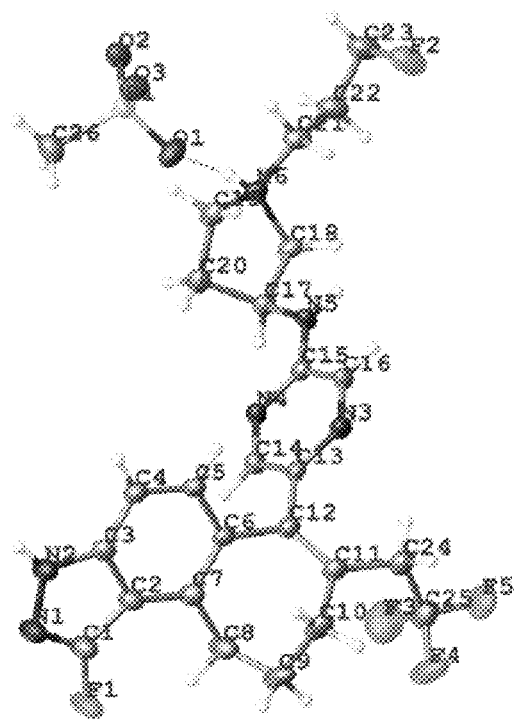
FIG. 9 shows a diagram of the single crystal structure of the compound of formula (II).

The present disclosure is described in detail by the examples below, but it does not mean that there are any adverse restrictions on the present disclosure. The compounds of the present disclosure can be prepared by a variety of synthetic methods known to those skilled in the art, including the specific embodiments listed below, the embodiments formed by their combination with other chemical synthesis methods, and equivalent alternatives known to those skilled in the art, preferred embodiments include but are not limited to the examples of the present disclosure. It will be apparent to those skilled in the art that various variations and improvements can be made to specific embodiments of the present disclosure without departing from the spirit and scope of the present disclosure.

Example 1: Preparation of Compound of Formula (I)

Preparation of Intermediate Compound 1-11

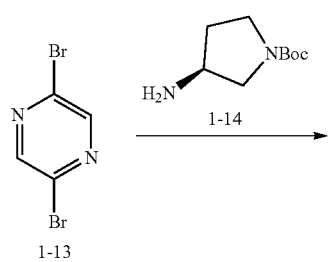

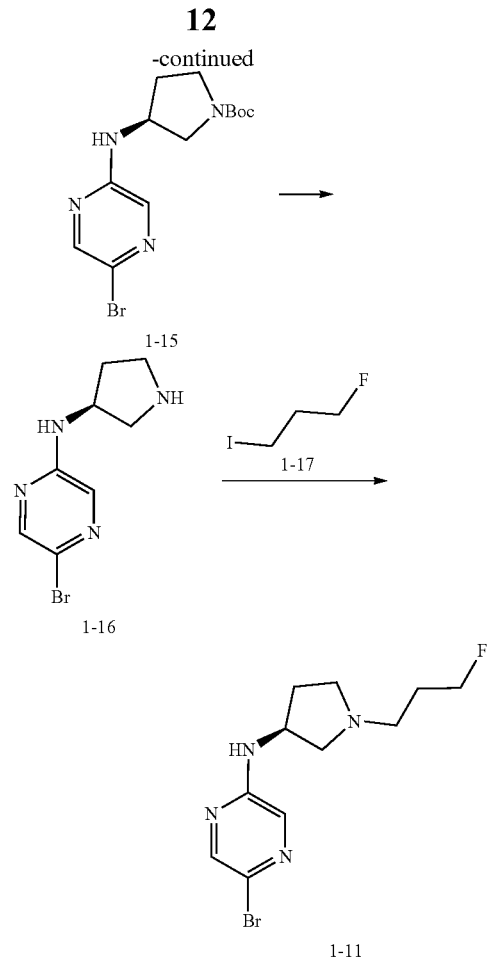

Step A: At 25° C., triethylamine (87.77 mL, 630.57 mmol) and 1-14 (78.30 g, 420.38 mmol) were sequentially added to a stirred solution of 1-13 (100.0 g, 420.38 mmol) in N-methylpyrrolidone (1000 mL). The resulting mixture was stirred at 130° C. (internal temperature) under a nitrogen atmosphere for 12 hours. Upon cooling to 25° C., water (1000 mL) was added to the stirred reaction mixture, and stirring was continued at 25° C. for 1 hour. The resulting suspension was filtered under reduced pressure using a Buchner funnel, and the filter cake was washed with water (200 mL×2). The filter cake was collected and dried under vacuum to obtain compound 1-15.

Step B: At 25° C., p-toluenesulfonic acid monohydrate (166.26 g, 874.08 mmol) was added to a stirred solution of 1-15 (100 g, 291.36 mmol) in tetrahydrofuran (700 mL). The mixture was stirred at 35° C. for 12 hours. The reaction mixture was concentrated under reduced pressure until no more liquid evaporated. The resulting crude product was dissolved in acetonitrile (300 mL) at 25° C. After the solution turned clear, methoxycyclopentane (1500 mL) was added thereto. The mixture was stirred at 25° C. for 12 hours. The resulting suspension was filtered under reduced pressure through a Buchner funnel. The filter cake was washed with methoxycyclopentyl ether (50 mL×2). The filter cake was collected and dried under vacuum to obtain compound 1-16.

Step C: At 25° C., anhydrous potassium phosphate (112.00 g, 527.65 mmol) and 1-17 (32.64 g, 173.62 mmol) were added to a stirred suspension of 1-16 (100 g, 170.21 mmol) in acetonitrile (1 L). The mixture was stirred at 40°

C. under a nitrogen atmosphere for 12 hours. The reaction mixture was concentrated under reduced pressure until no more liquid evaporated. 2-methyltetrahydrofuran (500 mL×3) and saturated sodium carbonate aqueous solution (400 mL) were added to the residue. After separation, the organic phase was added with saturated brine (300 mL×2). The organic phase was dried over anhydrous sodium sulfate, and filtered. The filtrate was concentrated under reduced pressure and dried to obtain compound 1-11. LCMS (ESI) m/z: 303/305 [M+H]$^+$.

Preparation of Compound of Formula (I)

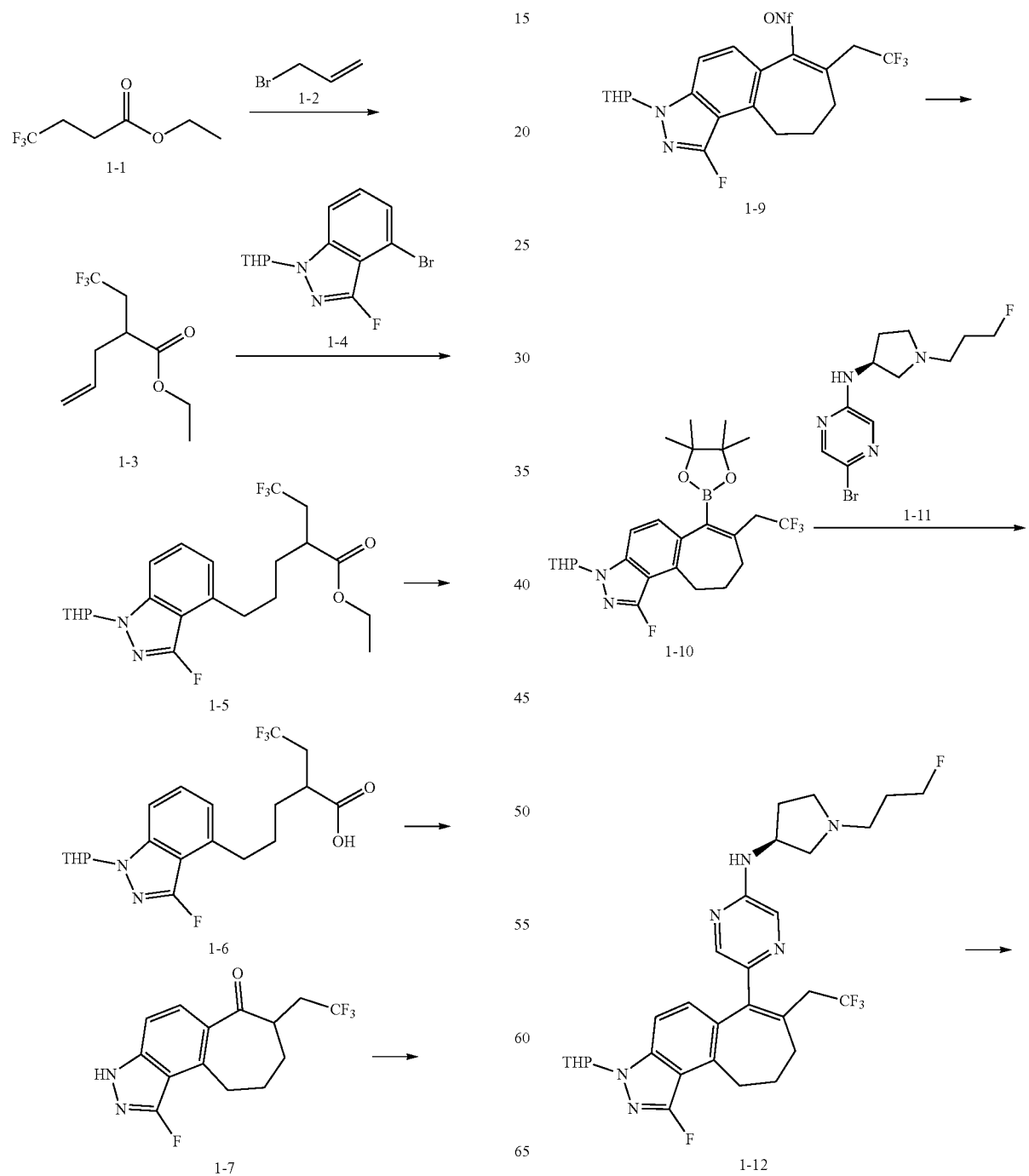

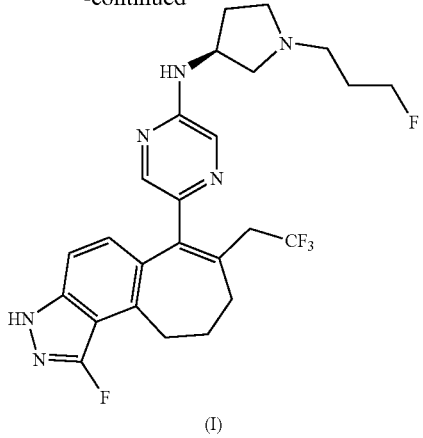

(I)

Step A: Under a nitrogen atmosphere at 0° C., a solution of n-butyllithium in hexane (2.5 mol/L, 28.21 mL3) was slowly added dropwise to a solution of N, N-diisopropylamine (7.73 g, 76.41 mmol) in tetrahydrofuran (100 mL). The reaction mixture was stirred at 0° C. for 0.5 hours and then freezed to −70° C. A solution of 1-1 (10 g, 58.78 mmol) in tetrahydrofuran (100 mL) was slowly added dropwise. After the addition was completed, the reaction mixture was stirred at −70° C. for 0.5 hours. Then, a solution of 1-2 (8.53 g, 70.53 mmol) in toluene (10 mL) was slowly added dropwise to the reaction mixture. After the addition was completed, the reaction mixture was further stirred at −70° C. for 3 hours. The reaction mixture was then added with a saturated ammonium chloride aqueous solution (200 mL) and extracted with ethyl acetate (100 mL×2). The organic phases were combined, and sequentially washed with saturated ammonium chloride aqueous solution (200 mL×2) and saturated brine (200 mL×2), dried over anhydrous sodium sulfate, filtered, and concentrated under reduced pressure to obtain the crude product. The crude product was purified by column chromatography (eluent: petroleum ether) to obtain compound 1-3.

Compound 1-3: $^1$HNMR (400 MHZ, CDCl$_3$) δ=5.82-5.59 (m, 1H), 5.15 (d, J=1.0 Hz, 1H), 5.13-5.09 (m, 1H), 4.19 (q, J=7.1 Hz, 2H), 2.82-2.74 (m, 1H), 2.69-2.53 (m, 1H), 2.50-2.40 (m, 1H), 2.39-2.30 (m, 1H), 2.30-2.17 (m, 1H), 1.32-1.27 (m, 3H).

Step B: Under a nitrogen atmosphere at 20° C., 9-borabicyclo[3.3.1]nonane (0.5 mol/L, 32.45 mL) was added to a solution of 1-3 (3.1 g, 14.75 mmol) in tetrahydrofuran (18 mL). The reaction mixture was stirred at 60° C. for 3 hours and then cooled to room temperature. Water (10 mL), 1-4 (3.53 g, 11.80 mmol), tetrakis(triphenylphosphine) palladium (0) (1.7 g, 1.47 mmol), and potassium phosphate (4.7 g, 22.12 mmol) were sequentially added to the reaction mixture. The mixture was stirred at 70° C. under a nitrogen atmosphere for 16 hours. The resulting reaction mixture was diluted with ethyl acetate (100 mL), then washed with saturated brine (200 mL×2), dried over anhydrous sodium sulfate, filtered, and concentrated under reduced pressure to obtain the crude product. The crude product was purified by column chromatography (eluent: petroleum ether/ethyl acetate=100/1 to 0/1) to obtain compound 1-5. LCMS (ESI) m/z: 431.1 [M+H]$^+$.

Step C: Sodium hydroxide (2.15 g, 53.83 mmol) was added to a mixed solution of 1-5 (6.7 g, 13.46 mmol) in methanol (75 mL) and water (25 mL). The mixture was stirred at 25° C. for 16 hours. The resulting reaction mixture was concentrated under reduced pressure to remove methanol. The residue was diluted with water (150 mL) and extracted with dichloromethane (100 mL×2). The aqueous phase was adjusted to pH=2 with hydrochloric acid (2 mol/L) and extracted with ethyl acetate (80 mL×4). The combined organic phases were washed with saturated brine (200 mL×2), dried over anhydrous sodium sulfate, filtered, and concentrated under reduced pressure to obtain compound 1-6.

Compound 1-6: $^1$HNMR (400 MHZ, CDCl$_3$) δ=7.34 (d, J=4.3 Hz, 2H), 6.99-6.90 (m, 1H), 5.59 (td, J=2.4, 9.3 Hz, 1H), 4.04 (br d, J=11.0 Hz, 1H), 3.73 (dt, J=2.9, 10.9 Hz, 1H), 2.97 (br t, J=7.1 Hz, 2H), 2.82-2.72 (m, 1H), 2.72-2.56 (m, 1H), 2.56-2.42 (m, 1H), 2.28-2.13 (m, 2H), 2.06-1.99 (m, 1H), 1.79-1.58 (m, 7H). LCMS (ESI) m/z: 403.1 [M+H]$^+$.

Step D: 1-6 (2.7 g, 6.54 mmol) was dissolved in polyphosphoric acid (30 mL), and the mixture was stirred at 110° C. for 16 hours. The resulting reaction mixture was diluted with water (300 mL) and extracted with ethyl acetate (100 mL×3). The combined organic phases were washed with a saturated aqueous solution of sodium carbonate (200 mL×2) and saturated brine (200 mL), dried over anhydrous sodium sulfate, filtered, and concentrated under reduced pressure to obtain compound 1-7. LCMS (ESI) m/z: 301.1 [M+H]$^+$.

Step E: 1-7 (2.7 g, 8.99 mmol) was dissolved in dichloromethane (50 mL), then p-toluenesulfonic acid monohydrate (855.26 mg, 4.5 mmol) and 3,4-dihydro-2H-pyran (1.13 g, 13.49 mmol) were added thereto. The mixture was stirred at 25° C. for 16 hours. The reaction mixture was concentrated under reduced pressure to obtain the crude product. The crude product was purified by column chromatography (eluent: petroleum ether/ethyl acetate=40/1 to 20/1) to obtain compound 1-8.

Compound 1-8: $^1$HNMR (400 MHZ, CDCl$_3$) δ=7.81 (dd, J=5.4, 8.9 Hz, 1H), 7.38 (td, J=2.0, 8.8 Hz, 1H), 5.59 (td, J=2.4, 9.2 Hz, 1H), 4.06-3.95 (m, 1H), 3.81-3.64 (m, 2H), 3.36-3.23 (m, 1H), 3.22-2.95 (m, 2H), 2.53-2.38 (m, 1H), 2.35-2.20 (m, 2H), 2.19-2.08 (m, 2H), 2.06-2.00 (m, 1H), 1.80-1.65 (m, 5H)). LCMS (ESI) m/z: 385.1 [M+H]$^+$.

Step F: Under a nitrogen atmosphere at −40° C., a solution of 1-8 (40 g, 104.07 mmol) in tetrahydrofuran (266 mL) was added dropwise to a solution of potassium bis(trimethylsilyl)amide in tetrahydrofuran (1 mol/L, 114.47 mL, 114.47 mmol). After the addition was completed, the mixture was stirred at −40° C. for 1 hour. At −40° C., perfluorobutanesulfonyl fluoride (20.11 mL, 114.47 mmol) was added dropwise to the reaction mixture. The temperature was gradually raised to 25° C. and the mixture was stirred for 12 hours. At 25° C., the reaction mixture was quenched by adding saturated ammonium chloride aqueous solution (1300 mL). The mixture was diluted with 500 mL of water and extracted with ethyl acetate (600 mL×3). The combined organic phases were washed with saturated brine (200 mL×2), dried over anhydrous sodium sulfate, filtered, and concentrated under reduced pressure to obtain the crude product (79.13 g). The crude product was stirred in ethanol (160 mL) at 25° C. for 12 hours. The resulting mixture was filtered and washed to obtain compound 1-9.

Step G: At 25° C., potassium carbonate (7.78 g, 56.27 mmol), triphenylphosphine (1.48 g, 5.63 mmol), and dichlorobis(triphenylphosphine) palladium (0) (1.84 g, 2.63 mmol) were added to a solution of 1-9 (25 g, 37.51 mmol) and bis(pinacolato)diboron (14.29 g, 56.27 mmol) in 1,4-dioxane (200 mL). The mixture was stirred at 90° C. under a nitrogen atmosphere for 12 hours. The resulting reaction mixture was filtered through diatomite and diluted with water (40 mL). The mixture was then extracted with ethyl acetate (50 mL×3). The combined organic phases were washed with saturated brine (40 mL×1), dried over anhydrous sodium sulfate, filtered, and concentrated under reduced pressure to obtain the crude product (30.43 g). The crude product was dissolved in acetonitrile (150 mL) and water (37.5 mL) and heated to 50° C. until it turned clear. The mixture was cooled to 25° C. and stirred for 12 hours. The resulting suspension was filtered under reduced pressure to collect the filter cake, yielding compound 1-10. LCMS (ESI) m/z: 495.2 $[M+H]^+$ Step H: At 25° C., potassium hydroxide (1.95 g, 34.71 mmol) and tetrakis(triphenylphosphine) palladium (0) (364.67 mg, 315.58 μmol) were added to a mixed solution of 1-11 (1.91 g, 6.31 mmol) and 1-10 (3.12 g, 6.31 mmol) in tetrahydrofuran (30 mL) and water (6 mL). The mixture was stirred at 60° C. under a nitrogen atmosphere for 12 hours. The resulting reaction mixture was diluted with water (20 mL) and extracted with dichloromethane (20 mL×3). The combined organic phases were washed with saturated brine (20 mL×1), dried over anhydrous sodium sulfate, filtered, and concentrated under reduced pressure to obtain the crude product. The crude product was purified by reverse-phase silica gel column chromatography (gradient elution with 0.1% aqueous ammonia solution and acetonitrile) to obtain compound 1-12. LCMS (ESI) m/z: 591.2 $[M+H]^+$.

Step I: At 20° C., trifluoroacetic acid (60 mL) was added to a solution of 1-12 (18 g, 7.87 mmol) in acetonitrile (180 mL). The mixture was stirred at 80° C. for 16 hours. The resulting reaction mixture was concentrated under reduced pressure until no more liquid evaporated. The residue was then adjusted to pH=8-10 with a sodium carbonate aqueous solution and extracted with dichloromethane. The combined organic phases were washed with saturated brine, dried over anhydrous sodium sulfate, filtered, and concentrated under reduced pressure to obtain the crude product. The crude product was purified by column chromatography (eluent: dichloromethane/methanol=10/1) to obtain the compound of formula (I). LCMS (ESI) m/z: 507.3 $[M+H]^+$

Example 2: Preparation of Crystal Form A of Compound of Formula (III)

5 g of the compound of formula (I) was taken, and 30 mL of acetonitrile was added to dissolve the compound. The solution was heated to 90° C., and added with fumaric acid (1.26 g) while stirring for 1 hour. The mixture was then slowly cooled to 20° C. and stirred for an additional 12 hours. The resulting suspension was filtered, and the filter cake was dried to obtain the crystal form A of the compound of formula (III). 1H NMR (400 MHZ, DMSO-$d_6$) δ=12.60 (s, 1H), 8.01 (d, J=1.2 Hz, 1H), 7.71 (d, J=0.8 Hz, 1H), 7.61 (br d, J=6.4 Hz, 1H), 7.28 (dd, J=2.4, 8.8 Hz, 1H), 6.87 (d, J=8.8 Hz, 1H), 6.64 (s, 2H), 4.61 (t, J=6.0 Hz, 1H), 4.50 (t, J=6.0 Hz, 1H), 4.46-4.35 (m, 1H), 3.54 (q, J=11.6 Hz, 2H), 3.13-2.94 (m, 4H), 2.85-2.70 (m, 4H), 2.45-2.24 (m, 3H), 2.10 (br t, J=6.8 Hz, 2H), 2.03-1.87 (m, 2H), 1.86-1.74 (m, 1H).

Example 3: Preparation of Crystal Form B of Compound of Formula (II)

1 g of the compound of formula (I) was taken and transferred to a 50 mL single-neck flask, and acetonitrile (9 mL) was added to dissolve the compound. After adding a magnetic stir bar, the solution was placed on a magnetic heating stirrer at 90° C. and stirred, and further added with a solution of methanesulfonic acid (155 μL) in acetonitrile (1 mL) while stirring at 90° C. The mixture was slowly cooled to 20° C. and stirred for an additional 12 hours. The resulting suspension was filtered, and the filter cake was dried to obtain the crystal form B of the compound of formula (II).

1 g of the compound of formula (I) was taken and transferred to a 50 mL single-neck flask, and ethyl acetate (10 mL) was added to dissolve the compound. After adding a magnetic stir bar, the solution was placed on a magnetic heating stirrer at 90° C. and stirred, and further added with a solution of methanesulfonic acid (155 μL) in ethyl acetate (1 mL) while stirring at 90° C. for 1 hour. The mixture was slowly cooled to 20° C. and stirred for an additional 12 hours. The resulting suspension was filtered, and the filter cake was dried to obtain the crystal form B of the compound of formula (II).

1 g of the compound of formula (I) was weighed and transferred to a 50 mL single-neck flask, and isopropyl acetate (9 mL) was added to dissolve the compound. After adding a magnetic stir bar, the solution was placed on a magnetic heating stirrer at 20° C. and stirred, and further added with a solution of methanesulfonic acid (155 μL) in isopropyl acetate (1 mL) while stirring at 20° C. The mixture was slowly cooled to 4° C. and stirred for an additional 17 hours. The resulting suspension was filtered, and the filter cake was dried to obtain the crystal form B of the compound of formula (II).

350 g of the crystal form B of the compound of formula (II) prepared as described above was added to a 5-liter single-neck flask, followed by the addition of dimethyl sulfoxide (455 mL). The mixture was heated to 60-70° C. until complete dissolution. At 60-70° C., isopropyl acetate (3 liters) was dropwise added over 1 hour. The mixture was stirred at this temperature for an additional hour. While stirring, the mixture was slowly cooled to 25-30° C. over 4-6 hours and then stirred at this temperature for 12 hours to obtain a milky suspension. The reaction mixture was filtered to obtain a pale yellow filter cake. The filter cake was washed thoroughly twice with isopropyl acetate (500 mL×2) while stirring, and was then filtered by suction at fixed temperature. The resulting filter cake was dried under vacuum to obtain the crude product. The crude product was then stirred with acetone (4.6 liters) at 55-60° C. for 16 hours, followed by filtration. The filter cake was again stirred with acetone (3.9 liters) at 55-60° C. for 16 hours and filtered. The filter cake was dried to obtain the crystal form B of the compound of formula (II). $^1$H NMR (400 MHZ, DMSO-$d_6$) δ=12.55 (s, 1H), 9.84-9.66 (m, 1H), 8.03 (br d, J=6.8 Hz, 1H), 7.72 (s, 1H), 7.70-7.53 (m, 1H), 7.24 (dd, J=2.0, 8.7 Hz, 1H), 6.81 (d, J=8.8 Hz, 1H), 4.60 (q, J=5.6 Hz, 1H), 4.52-4.43 (m, 2H), 4.05-3.62 (m, 2H), 3.61-3.37 (m, 4H), 3.29 (br s, 2H), 3.23-2.99 (m, 1H), 2.96 (br t, J=6.8 Hz, 2H), 2.40-2.31 (m, 5H), 2.14-1.94 (m, 6H).

Example 4: Preparation of Crystal Form C of Compound of Formula (I)

4 g of the compound of formula (I) was taken, and 12 mL of isopropyl acetate was added to dissolve the compound. The solution was then stirred while 30 mL of n-heptane was slowly added thereto. The mixture was stirred at 25° C. for 12 hours. The resulting suspension was filtered, and the filter cake was dried to obtain the crystal form C of the compound of formula (I). $^1$H NMR (400 MHZ, CD$_3$OD) δ=7.92 (d, J=1.3 Hz, 1H), 7.72 (d, J=1.3 Hz, 1H), 7.18 (dd, J=2.4, 8.8 Hz, 1H), 6.85 (d, J=8.8 Hz, 1H), 4.55 (t, J=5.9 Hz, 1H), 4.47-4.37 (m, 2H), 3.41-3.33 (m, 2H), 3.08 (br t, J=7.0 Hz, 2H), 2.98 (dd, J=7.1, 9.9 Hz, 1H), 2.79 (dt, J=6.3, 8.6 Hz, 1H), 2.68-2.58 (m, 3H), 2.54 (dd, J=4.9, 10.0 Hz, 1H), 2.46-2.30 (m, 3H), 2.19-2.11 (m, 2H), 2.00-1.84 (m, 2H), 1.82-1.71 (m, 1H). LCMS (ESI) m/z: 507.2 [M+H]$^+$ Experimental Example 1: Biological Testing (1) ERα Binding Assay: Assessment of the Activity of the Compound of Formula (I) Via Radioactive Ligand Binding Assay Experimental Materials:
Estrogen receptor α (ERα)
Source: Human recombinant insect Sf9 cells
Ligand: 0.5 nM [$^3$H] estradiol
Vehicle: 1.0% DMSO
Nonspecific ligand: 1.0 UM diethylstilbestrol
Incubation time/Temperature: 2 hours at 25° C.
Specific binding: 85%
Incubation buffer: 10 mM Tris-HCl, pH 7.4, 0.1% BSA, 10% glycerol, 1 mM DTT
Quantification method: Radioactive ligand binding
Kd: 0.2 nM
Significance criterion: ≥50% maximum activation or inhibition
Bmax: 1400 pmol/mg protein Experimental Method:
The method employed in this study was adopted from scientific literature (Obourn, J. D. et al., Biochemistry, 1993, 32, 6229-6236).

Data Analysis:
The IC$_{50}$ values were obtained using MathIQ™ software (ID Business Solutions Ltd., UK) employing a nonlinear, least-squares regression method. The presented inhibition constant (Ki) was calculated using the Cheng and Prusoff equation (Cheng, Y., Prusoff, W. H., Biochem. Pharmacol. 22:3099-3108, 1973) based on the experimentally determined IC$_{50}$ of the test compound, the concentration of the radioactive ligand used in the assay, and the historical value of the ligand's K$_D$ (determined experimentally by Eurofins Panlabs, Inc.). As shown, the Hill coefficient (nH), which defines the slope of the competitive binding curve, was calculated using MathIQ™. A significant deviation of the Hill coefficient from the value of 1 may indicate that the binding displacement does not adhere to the law of mass action for a single binding site. If the IC$_{50}$, K$_i$, and/or n$_H$ data do not include the standard error of the mean (SEM), the data may be insufficient for quantification and should be interpreted with caution (K$_i$, IC$_{50}$, n$_H$).

TABLE 4

Results of ERα binding assay

| Compound name | Species | Repetitions | Concentration | Inhibition rate (%) | IC$_{50}$ | K$_i$ | n$_H$ |
|---|---|---|---|---|---|---|---|
| Compound of formula (I) | Human | 2 | 1 μM | 97 | 0.36 nM | 0.10 nM | 1.22 |
| | | | 0.2 μM | 97 | | | |
| | | | 0.04 μM | 98 | | | |
| | | | 8 nM | 97 | | | |
| | | | 1.6 nM | 84 | | | |
| | | | 0.32 nM | 48 | | | |
| | | | 0.064 nM | 9 | | | |
| | | | 12.8 pM | −4 | | | |

Conclusion:
The compound of the present disclosure exhibits relatively strong binding affinity to ERα in vitro.

(2) HEK293/GAL4/ERα Antagonist Assay

Experimental Materials:

TABLE 5

| Name | Manufacturer |
|---|---|
| DMEM medium | Viva Cell |
| DMEM medium without phenol red | Basal Media |
| Fetal bovine serum | Biosera |
| Charcoal-stripped serum | Biosun |
| DMSO | Sinopharm |
| 96-Well cell culture plate | Corning |
| 96-Well compound plate | Shanghai Jingrao Biotechnology Co., Ltd. |
| Bright-Glo ™ Luciferase Assay | Promega |
| Cell culture dish | NEST |
| Estradiol | TargetMol |
| EDTA | Basal Media |

Cell Information and Culture Conditions:

TABLE 6

| Cell name | Cell type | Cell source | Medium | Culture conditions |
|---|---|---|---|---|
| HEK293/GAL4/ERα | Overexpression cells | constructed by Wuhan Heyan Biomedical Technology | DMEM with 10% fetal bovine serum (i.e., 450 mL DMEM and 50 mL fetal bovine serum in 500 mL medium) | 37° C., 5% CO$_2$ |

Experimental Medium:
DMEM (without phenol red) containing 10% charcoal-stripped serum (i.e., 450 mL DMEM and 50 mL charcoal-stripped serum in 500 mL medium)

Bright-Glo Detection Reagents:
The Bright-Glo™ Luciferase Assay Kit includes two reagents:
Bright-Glo™ Buffer
Bright-Glo™ Substrate Prior to use, equilibrate both reagents to room temperature (25° C.), then mix them together. The reagent mixture can be used once it is completely dissolved. Unused Bright-Glo reagent can be stored at −20° C. for future use.

Experimental Design:

The antagonistic effect of the compound of formula (I) on ERα, was analyzed using triplicate wells with compound concentration ranging from 200 nM to 0.00256 nM.

Experimental Steps:

1) The HEK293/GAL4/ERα cell suspension was collected and centrifuged at 1000 rpm for 5 minutes. The supernatant was discarded, and the cells were resuspended in pre-warmed experimental medium. After counting, the cell suspension was diluted with experimental medium. 40000 cells per well were seeded into a 96-well cell culture plate, with 80 μL of cell suspension per well. The plate was incubated overnight at 37° C. in a 5% $CO_2$ incubator.

2) On the day of the experiment, 10 μL of compound working solution was added to each well according to the compound layout map. The cell plate was incubated at 37° C. in a 5% $CO_2$ incubator for 1 hour. Subsequently, 10 μL of assay medium containing 10 nM estradiol was added to each well. For blank controls, 10 μL of assay medium was added. A final estradiol concentration of 1 nM was ensured. The cell plate was further incubated at 37° C. in a 5% $CO_2$ incubator for 24 hours.

3) After the incubation period, the cell supernatant was removed, and 50 μL of Bright-Glo detection reagent was added to each well. The plate was incubated at 25° C. for 2 minutes. After incubation, the luminescence signal was then detected using an EnVision plate reader.

Data Analysis:

The inhibition rate of ERα following compound treatment was calculated using the following formula: % inhibition=100−($RFU_{compound}$−$RFU_{blank\ control}$)/($RFU_{negative\ control}$−$RFU_{blank\ control}$)×100% Negative control: cells treated with 1 nM estradiol; blank control: cells not treated with estradiol. GraphPad Prism software was used to plot the data and calculate the $IC_{50}$ values for the compound.

Experimental Results

The $IC_{50}$ values for the antagonistic effect of the compound of formula (I) on HEK293/GAL4/ERα cells are shown in Table 7.

TABLE 7

Summary of the antagonistic effect of the compound on HEK293/GAL4/ERα

| | | $IC_{50}$ (nM) | | |
| --- | --- | --- | --- | --- |
| Cell | Compound | N = 1 | N = 2 | Mean ± SD |
| HEK293/GAL4/ERα | Formula (I) | 0.096 | 0.075 | 0.0857 ± 0.0103 |

Experimental Conclusion:

The compound of formula (I) exhibits a significant antagonistic effect on the transcriptional function of HEK293/GAL4/ERα cells.

(3) ERα Degradation Assay in MCF-7, T-47D, and CAMA-1 Cells

Experimental Materials:

TABLE 8

| Reagent name | Brand |
| --- | --- |
| RPMI-1640 | Gibco |
| EMEM | ATCC |
| Fetal Bovine Serum | ExCell Bio |
| TrypLE | Gibco |
| Dimethyl Sulfoxide | SIGMA |
| DPBS | CORNING |
| Anti-Anti (100 X) | Gibco |
| IRDye 800CW Goat anti-Rabbit 0.5 mg | Licor |
| DRAQ5 1000 μL | BioStatus |
| Estrogen Receptor alpha Monoclonal Antibody (SP1) 500 μL | Invertrogen |
| Intercept Blocking Buffer | Licor |
| Triton X-100 | SIGMA |
| TWEEN 20 | SIGMA |

Cell Information and Culture Conditions:

TABLE 9

| Cell name | Complete medium | Cells per well | Total volume of cell suspension (mL) | Total number of cells |
| --- | --- | --- | --- | --- |
| MCF-7 | RPMI-1640 medium + 10% FBS + 1% Anti-Anti | 10000 | 6.00 | 2.00E+06 |
| T-47D | RPMI-1640 medium + 10% FBS + 1% Anti-Anti | 25000 | 6.00 | 5.00E+06 |
| CAMA-1 | EMEM medium + 10% FBS + 1% Anti-Anti | 40000 | 6.00 | 8.00E+06 |

Preparation of Detection Reagents:

Preparation of TritonX-100: TritonX-100 was diluted with DPBS to a final concentration of 1.00% TritonX-100 (100-fold dilution).

Preparation of blocking buffer with 0.100% Tween 20: Tween 20 was diluted with blocking buffer to achieve a final concentration of 0.100% Tween 20 (1000-fold dilution).

Preparation of primary antibody dilution solution: The primary antibody (Estrogen Receptor alpha Monoclonal Antibody (SP1)) storage solution was diluted 1000 times with a blocking buffer containing 0.100% Tween-20 to obtain the primary antibody dilution solution.

Preparation of secondary antibody and DRAQ5 mixture: The secondary antibody (LI-COR-926-32211, 1:1000 dilution) and DRAQ5 (DR51000, 1:2000 dilution) were diluted with a blocking buffer containing 0.100% Tween-20 and mixed thoroughly.

Experimental Steps:

1) The complete culture medium was aspirated from the culture flask, followed by the addition of an appropriate amount of trypsin for rinsing. The trypsin solution was then aspirated to remove residual serum.
2) Subsequently, an appropriate amount of trypsin was added for a second rinse and aspirated. The culture flask was placed in an incubator for 2-3 minutes, then removed, and gently agitated to detach the cells.
3) The cells were resuspended in fresh complete culture medium and counted using a cell counter.
4) The cell suspension was prepared according to the required plating density.
5) A volume of 30.0 μL of the cell suspension was added to each well of a 384-well plate.
6) The experimental plate was placed in a centrifuge and centrifuged at 1000 rpm for 1 minute.
7) The experimental plate was then incubated overnight in a cell incubator.
8) According to the sample addition diagram of experimental plate (refer to 3.5.1), 20.0 μL of the diluted test sample was added to each well. The final concentration of DMSO in the reaction system was 1.00%.
9) The experimental plate was placed in a centrifuge and centrifuged at 1000 rpm for 1 minute.
10) The plate was incubated at 37° C. with 5% $CO_2$ for 4 hours.
11) The plate was retrieved and equilibrated at room temperature for 10 minutes, and the medium was removed from the wells.
12) A volume of 100 μL of 4.00% PFA was added to each well for fixation at room temperature for 40 minutes.
13) The liquid was discarded from the plate, and 100 μL of 1×PBS was added to each well using a multidrop, the wash step was repeated twice.
14) Subsequently, 50 μL of ice-cold PBS containing 0.1% TritonX-100 was added to permeabilize the cells, which was then left to stand at room temperature for 15 minutes.
15) The liquid was discarded, and 100 μL of PBS was added to each well using a multidrop, the wash step was repeated five times.
16) 50 μL of blocking buffer containing 0.1% Tween-20 (LI-COR-927-40000) was added to each well, and the blocking was processed at room temperature for 1 hour.
17) The blocking buffer was discarded.
18) 25 μL of primary antibody dilution solution was added to each well of the 384-well plate. The plate was incubated at 4° C. overnight.
19) The primary antibody solution in the plate was discarded, and the plate was washed five times with PBS using a multidrop.
20) A mixture of 25 μL of secondary antibody and DRAQ5 was added to each well, and incubated at room temperature for 1 hour.
21) The plate was washed five times with PBS using a multidrop.
22) The plate was washed with $ddH_2O$ twice, and patted dry.
23) The plate was subsequently read using the Odyssey infrared imaging system.

Data Analysis

High control group mean value: the mean value of the high control group was calculated. Low control group mean value: the mean value of the low control group was calculated. High control group standard deviation (SD): the standard deviation of the high control group was calculated. Low control group standard deviation (SD): the standard deviation of the low control group was calculated.

High control group coefficient of variation (CV)=(High control group SD÷High control group mean value)×100

Low control group coefficient of variation (CV)=(Low control group SD÷Low control group mean value)×100

Experimental window=High control group mean value÷Low control group mean value

Z value=1−[3×(High control group SD+Low control group SD)÷(High control group mean value−Low control group mean value)]

Inhibition rate (%)=(1−(Signal value of experimental well−Low control group mean value)/(High control group mean value−Low control group mean value))×100

The $IC_{50}$ values were calculated using GraphPad Prism 7.0, a data analysis software.

The analysis quality control standards were as follows: experimental window>2; Z-value>0.5; consistency in data for reference/positive compounds.

Experimental Results:

This experiment evaluated the effect of compound of formula (I) on the expression of ERα protein in MCF-7, T-47D, and CAMA-1 cells. The expression levels of ERα protein were detected using the ICW assay after 4 hours of drug treatment. The results are as follows:

TABLE 10

Summary of the degradation effect of compound on ERα

| Cell | $IC_{50}$ (nM) |
| --- | --- |
| MCF-7 | 0.235 |
| T-47D | 0.780 |
| CAMA-1 | 1.25 |

Experimental Conclusion:

The compound of formula (I) demonstrates significant degradation effects on ERα in various breast cancer cell lines.

(4) MCF-7, T-47D, and CAMA-1 Cell Proliferation Inhibition Assay

Experimental Materials:

TABLE 11

| Name | Manufacturer |
| --- | --- |
| Estradiol | TargetMol |
| 0.25% Trypsin | BasalMedia |
| Fetal bovine serum | Biosera |
| Charcoal-stripped serum | Biosun |
| RPMI-1640 | Viva Cell |
| RPMI-1640 medium without phenol red | BasalMedia |
| EMEM | Wisent |
| EMEM medium without phenol red | Wisent |
| Penicillin-Streptomycin solution (Dual antibiotic) | Base Media |
| NEAA | Wisent |
| Sodium pyruvate | Macklin |
| DMSO | Sinopharm |
| 96-Well cell culture plate | Corning |
| 384-Well cell culture plate | PerkinElmer |
| CellTiter-Glo ® Luminescent Cell Viability Assay | Promega |
| Cell culture dish | NEST |

Cell Information and Culture Conditions:

TABLE 12

| Cell name | Cell source | Medium | Culture conditions |
| --- | --- | --- | --- |
| MCF-7 | Procell | EMEM containing 10% fetal bovine serum, 1% dual antibiotic (500 mL culture medium containing 445 mL EMEM, 50 mL fetal bovine serum, 5 mL dual antibiotic) | 37° C., 5% $CO_2$ |
| CAMA-1 | Nanjing cobioer | EMEM containing 10% fetal bovine serum, 1% NEAA, 1 mM sodium pyruvate, 1% dual antibiotic (500 mL culture medium containing 435 mL EMEM, 50 mL fetal bovine serum, 5 mL NEAA, 5 mL 100 mM sodium pyruvate, 5 mL dual antibiotic) | 37° C., 5% $CO_2$ |
| T-47D | Nanjing cobioer | RPMI-1640 containing 10% fetal bovine serum, 1% dual antibiotic (500 mL culture medium containing 445 mL RPMI-1640, 50 mL fetal bovine serum, 5 mL dual antibiotic) | 37° C., 5% $CO_2$ |

Starvation Medium:

CAMA-1: EMEM (without phenol red) containing 10% charcoal-stripped serum (500 mL culture medium containing 440 mL EMEM, 50 mL charcoal-stripped serum, 5 mL NEAA, 5 mL 100 mM sodium pyruvate).

T-47D: RPMI-1640 (without phenol red) containing 10% charcoal-stripped serum (500 mL culture medium containing 450 mL RPMI-1640, 50 mL charcoal-stripped serum).

Experimental Design

The inhibitory effect of the test compound of formula (I) on the proliferation of MCF-7, CAMA-1, and T-47D cells was analyzed. For MCF-7 cells, ten concentration gradients ranging from 100 nM to 0.0003815 nM were tested, with three replicates for each concentration. For CAMA-1 cells, nine concentration gradients ranging from 100 nM to 0.001526 nM were tested, also with three replicates for each concentration. For T-47D cells, nine concentration gradients ranging from 2 μM to 0.00512 nM were tested, with three replicates for each concentration. Each experiment was conducted twice independently.

Experimental Steps:

MCF-7 Cells:

MCF-7 cells that reached 80% cell fusion were digested using trypsin, centrifuged, resuspended, and counted. Cell suspensions were prepared using the corresponding culture medium, and 45 μL of the suspension was added to each well of a 384-well plate. The plate was then incubated at 37° C. in a cell incubator with 5% $CO_2$. The test compound of formula (I) was dissolved in DMSO to an initial concentration of 20 μM and subjected to a 4-fold serial dilution to achieve ten different concentrations. After overnight incubation, the diluted compound was further diluted with the corresponding cell culture medium. The resulting mixture was transferred to the respective wells of the cell plate, starting with a final concentration of 100 nM, followed by a 4-fold serial dilution to achieve ten concentrations. The positive control wells contained 2 μM fulvestrant. The plate was mixed, centrifuged, and incubated at 37° C. in a cell incubator with 5% $CO_2$ for the specified number of days according to the above table.

T-47D Cells:

The T-47D cells were treated with starvation medium for three days, followed by trypsin digestion, centrifugation, resuspension, and counting. Cell suspensions were prepared using the corresponding culture medium, and 40 μL of the suspension was added to each well of a 384-well plate. The plate was then incubated at 37° C. in a cell incubator with 5% $CO_2$. The test compound of formula (I) was dissolved in DMSO to an initial concentration of 400 μM and subjected to a 5-fold serial dilution to achieve nine different concentrations. After overnight incubation, the diluted compound was further diluted with the corresponding cell culture medium. The resulting mixture was transferred to the respective wells of the cell plate, starting with a final concentration of 2 μM, followed by a 5-fold serial dilution to achieve nine concentrations. The positive control wells contained 2 μM fulvestrant, and 1 nM estradiol was added to the entire plate. The plate was mixed, centrifuged, and incubated at 37° C. in a cell incubator with 5% $CO_2$ for the specified number of days according to the above table.

CAMA-1 Cells:

The CAMA-1 cells were treated with starvation medium for three days, followed by trypsin digestion, centrifugation, resuspension, and counting. Cell suspensions were prepared using the corresponding culture medium, and 80 μL of the suspension was added to each well of a 96-well plate. The plate was then incubated at 37° C. in a cell incubator with 5% $CO_2$. The test compound of formula (I) was dissolved in DMSO to an initial concentration of 20 μM and subjected to a 4-fold serial dilution to achieve nine different concentrations. After overnight incubation, the diluted compound was further diluted with the corresponding cell culture medium.

The resulting mixture was transferred to the respective wells of the cell plate, starting with a final concentration of 100 nM, followed by a 4-fold serial dilution to achieve nine concentrations. The positive control wells contained 2 μM fulvestrant, and 1 nM estradiol was added to the entire plate. The plate was mixed, centrifuged, and incubated at 37° C. in a cell incubator with 5% $CO_2$ for the specified number of days according to the above table.

After incubation for the specified time, the cell culture plate was removed, and the CTG reagent was added. The plate was thoroughly mixed, centrifuged, and incubated at room temperature for 10 minutes. The readings were taken using the Envision multi-label analyzer. Data analysis:

The data were analyzed using the following formula to calculate cell viability after compound treatment: % inhibition rate=100−($RFU_{compound}$−$RFU_{positive\ control}$)/($RFU_{negative\ control}$−$RFU_{positive\ control}$)×100%. Positive control: cells treated with 2 μM fulvestrant; negative control: cells treated with 0.5% DMSO. Prism 5 was used to plot the data and calculate the $IC_{50}$ values of the compound. The formula for calculating $IC_{50}$ is log (inhibitor) vs. response-Variable slope.

Experimental Results:

The inhibitory effect of the test compound of formula (I) on the proliferation of MCF-7, CAMA-1, and T-47D cells was analyzed. Three replicates were set, and the experiments were independently repeated twice.

The $IC_{50}$ values of the compound on the inhibition of cell proliferation are presented in the table below.

TABLE 13

Inhibitory effect of the compound on cell proliferation

| Cell name | $IC_{50}$ (nM) | | |
|---|---|---|---|
| | First experiment | Second experiment | Mean ± SD |
| MCF-7 | 0.19 | 0.16 | 0.18 ± 0.013 |
| CAMA-1 | 1.19 | 1.39 | 1.29 ± 0.10 |
| T-47D | 1.98 | 2.71 | 2.35 ± 0.37 |

Experimental Conclusion:

The compound of formula (I) exhibits significant in vitro antiproliferative activity in MCF-7, CAMA-1, and T-47D cells.

(5) HCC1428 and MDA-MB-134VI Cell Proliferation Inhibition Assay

Experimental Materials:

TABLE 14

| Reagent | Brand |
|---|---|
| DMSO | Sigma |
| MDA-MB-134VI | COBIOER |
| HCC1428 | COBIOER |
| DMEM | ATCC |
| RPMI1640 | ATCC |
| TrypLE ™ Express Enzyme (1X), no phenol red | Gibco |
| Penicillin-streptomycin | Gibco |
| DPBS | Gibco |
| CellTiter Glo assay kit (CTG) | Promega |
| T75 flask | Corning |
| 96-well, Flat Bottom | Corning |

Experimental Design:

The initial concentration of the compound of formula (I) was set at 200 nM, followed by 4-fold serial dilutions to achieve ten concentration gradients.

Experimental Steps

Mda-Mb-134VI Cells:
1) MDA-MB-134VI cells were cultured in DMEM complete growth medium containing 20% FBS and 1% PenStrep.
2) When the cells in a T75 culture flask reached 80-90% cell fusion, they were digested with trypsin and collected. The cell passages used were the eighth generation for the first independent experiment and the sixth generation for the second independent experiment.
3) The cells were centrifuged at 1000 rpm, resuspended in complete medium, and counted. The cell densities were $3.60 \times 10^6$ cells/mL for the first experiment and $1.93 \times 10^6$ cells/mL for the second experiment, with viability both exceeding 95%.
4) Cell suspensions were prepared in complete medium at a density of $4.00 \times 10^4$ cells/mL for both experiments. Cells were seeded at 8000 cells/195 μL per well in a 96-well round-bottom plate and incubated overnight at 37° C. in a 5% $CO_2$ incubator.
5) The next day, 5 μL of the diluted compound was added to each well, ensuring a final DMSO concentration of 0.1%. DMSO wells served as the high control, and medium-only wells served as the low control.
6) MDA-MB-134VI cells were incubated at 37° C. in a 5% $CO_2$ incubator for 10 days.
7) The cells were taken out and equilibrated to room temperature, then centrifuged at 1000 rpm for 5 minutes, and 100 μL of the supernatant was discarded from each well. 100 μL of CellTiter-Glo® reagent was added to each well. The plates were incubated at room temperature in the dark for 30 minutes.
8) Luminescence values were read using a BMG plate reader.

Two independent experiments were conducted following the aforementioned steps.

HCC1428 Cells:
1) HCC1428 cells were cultured in RPMI 1640 complete growth medium containing 10% FBS and 1% PenStrep.
2) When the cells in a T75 culture flask reached 80-90% cell fusion, they were digested with trypsin and collected. The cell passages used were the seventh generation for the first independent experiment and the thirteenth generation for the second independent experiment.
3) The cells were centrifuged at 1000 rpm, resuspended in complete medium, and counted. The cell densities were $1.30 \times 10^6$ cells/mL for the first experiment and $9.50 \times 10^5$ cells/mL for the second experiment, with viability both exceeding 95%.
4) Cell suspensions were prepared in complete medium at a density of $1.25 \times 10^4$ cells/mL for both experiments. Cells were seeded at 2500 cells/195 μL per well in a 96-well round-bottom plate and incubated overnight at 37° C. in a 5% $CO_2$ incubator.
5) 5 μL of the diluted compound was added to each well, ensuring a final DMSO concentration of 0.1%. DMSO wells served as the high control, and medium-only wells served as the low control.
6) HCC1428 cells were incubated at 37° C. in a 5% $CO_2$ incubator for 7 days.
7) The cells were taken out and equilibrated to room temperature, centrifuged at 1000 rpm for 5 minutes, and 100 μL of the supernatant was discarded from each well. 100 μL of CellTiter-Glo® reagent was added to each well. The plate was incubated at room temperature in the dark for 30 minutes.

8) Luminescence values were read using a BMG plate reader.

Two independent experiments were conducted following the aforementioned steps.

Data Analysis

The inhibition rate for each test solution was calculated by setting the negative control's reading as 0% inhibition and the positive control's reading as 100% inhibition.

$$\% \text{ Inhibition rate} = \frac{\lfloor \overline{\text{Data}}_{High\ ctrl} - \text{Data}_{sample} \rfloor}{\lfloor \overline{\text{Data}}_{High\ ctrl} - \text{Data}_{Low\ ctrl} \rfloor} * 100$$

$\overline{\text{Data}}_{High\ ctrl}$: the average signal value of DMSO control wells.

$\overline{\text{Data}}_{Low\ ctrl}$: the average signal value of medium-only control wells.

The $IC_{50}$ (half-maximal inhibitory concentration) of the compound was obtained using the following nonlinear fitting formula:

$$Y = \text{Bottom} + (\text{Top} - \text{Bottom})/(1 + 10\wedge((\text{Log}IC_{50} - X) * HillSlope))$$

X: the logarithmic value of the compound concentration

Y: the inhibition rate of the compound (% inh)

The Z' factor was calculated using the following equation:

$$Z' = 1 - 3 * (SD\_H + SD\_L)/(Ave\_H - Ave\_L)$$

SD represented the standard deviation and AVE represented the average value.

Experimental Results

The inhibitory effects of the compound of formula (I) on the proliferation of MDA-MB-134VI and HCC1428 cells were analyzed in this experiment. The $IC_{50}$ values of the compound on the inhibition of cell proliferation are presented in the table below.

TABLE 15

Inhibitory effects of the compound on cell proliferation

| Cell name | $IC_{50}$ (nM) | | |
|---|---|---|---|
| | First experiment | Second experiment | Mean ± SD |
| MDA-MB-134VI | 0.12 | 0.49 | 0.31 ± 0.26 |
| HCC1428 | 0.49 | 1.34 | 1.55 ± 0.99 |

Experimental Conclusion:

The compound of formula (I) exhibits significant in vitro anti-proliferative activity against MDA-MB-134VI and HCC1428 cells.

(6) Proliferation Inhibition Assay for MCF-7 Mutant Cell Lines MCF-7 ESR1-Y537S and MCF-7 ESR1-D538G Experimental Materials:

TABLE 16

| Name | Manufacturer |
|---|---|
| RPMI-1640 (without phenol) | Thermo |
| Dulbecco's PBS | Hyclone |
| EMEM | ATCC |
| FBS | Hyclone |
| L-Glutamine | GIBCO |
| Non Essential Amino Acids (NEAA) | GIBCO |
| Antibiotic-antimycotic | GIBCO |
| 0.25% Trypsin | GIBCO |
| DMSO | SIGMA |

Cell Information and Culture Conditions:

TABLE 17

| Cell name | Cell source | Culture method |
|---|---|---|
| MCF-7 ESR1-Y537S | WuXi | EMEM + 10% FBS + 2 mM L-Glutamine + 0.1% NEAA |
| MCF-7 ESR1-Y537S | WuXi | EMEM + 10% FBS + 2 mM L-Glutamine + 0.1% NEAA |

Experimental Methods and Procedures:

1. Cell Culture

The tumor cell lines were cultured in an incubator at 37° C. with 5% $CO_2$. Regular passaging was performed, and cells in the logarithmic growth phase were selected for plating.

2. Cell Plating

1) Cells were stained with trypan blue and viable cells were counted.

2) Cells were washed once with PBS and resuspended in RPMI 1640+10% FBS medium without phenol red. The concentration was adjusted to an appropriate one.

3) 135 μL of the cell suspension per well was added to a culture plate, and cell-free culture medium was added to the blank control well.

4) The plates were incubated overnight at 37° C. with 5% $CO_2$ and 100% relative humidity.

3. Preparation of 10× Compound Working Solution and Treatment of Cells

1) Preparation of 10× compound working solution: 199 μL of cell culture medium was added to V-bottom 96-well plates. From a 2000× compound storage plate, 1 μL of the compound was added to the 96-well plate containing cell culture medium. 1 μL of DMSO was added to vehicle control and blank control. After the compound or DMSO was added, blowing with a pipette and mixing well were carried out.

2) Administration: 15 μL of the 10× compound working solution was added to the cell culture plate as indicated in Table 1. To vehicle control and blank control was added 15 μL of DMSO-cell culture medium mixture. The final concentration of DMSO was 0.05%.

3) The 96-well cell plate was returned to the incubator for further culture, and cell viability was assessed after 7 days.

4. Cell Viability Detection Using CellTiter-Glo Luminescent Assay:

The following steps were conducted in accordance with the instructions of the Promega CellTiter-Glo Luminescent Cell Viability Assay Kit (Promega-G7573).
1) CellTiter-Glo buffer was thawed and brought to room temperature.
2) CellTiter-Glo substrate was also brought to room temperature.
3) CellTiter-Glo buffer was added to a bottle of CellTiter-Glo substrate to dissolve the substrate, thereby preparing CellTiter-Glo working solution.
4) The mixture was slowly vortexed and shaken to ensure that the substrate was completely dissolved.
5) The cell culture plate was removed and allowed to equilibrate to room temperature for 30 minutes.
6) 75 μL (equal to half the volume of cell culture medium in each well) of CellTiter-Glo working solution was added to each well. The cell plate was wrapped in aluminum foil to be protected from light;
7) The culture plate was shaken on an orbital shaker for 2 minutes to induce cell lysis.
8) The plate was then left at room temperature for 10 minutes to stabilize the luminescent signal.
9) The luminescent signal was detected on a 2104 EnVision plate reader.

Data Analysis:

The inhibition rate (IR) of the compound was calculated using the following formula:

$$IR (\%) = \left(1 - (RLU_{compound} - RLU_{blank\ control})/(RLU_{vehicle\ control} - RLU_{blank\ control})\right) * 100\%.$$

Inhibition rates for different concentrations of the compound were calculated in Excel. The inhibition curves were then fitted using the "log (inhibitor) vs. response—Variable slope" model in GraphPad Prism (version 6.02.328) software to determine the relevant parameters.

The relative $IC_{50}$ value represents the concentration required to reduce the response to half the distance between the top and bottom plateaus of the curve. Similarly, the relative $IC_{90}$ value represents the concentration required to reduce the response to 90% of the distance between the top and bottom plateaus of the curve.

Experimental Results:

The inhibitory effects of the compound of formula (I) on the proliferation of the two mutant MCF-7 cell lines were analyzed in this experiment. The $IC_{50}$ values of the compound on the inhibition of cell proliferation are presented in the table below.

TABLE 18

Inhibitory effect of the compound on cell proliferation

| Cell line | Relative $IC_{50}$ (nM) | Relative $IC_{90}$ (nM) |
|---|---|---|
| MCF-7 ESR1-Y537S | 11.17 | 100.53 |
| MCF-7 ESR1-D538G | 2.90 | 26.1 |

Experimental Conclusion:

The compound of formula (I) exhibits significant in vitro anti-proliferative activity against the MCF-7 cells with ESR1-Y537S and ESR1-D538G mutations.

Experimental Example 2: Evaluation of DMPK Properties (1) Study on the Inhibition of Cytochrome P450 Isozymes Experimental Materials:

TABLE 19

| Name | Manufacturer |
|---|---|
| HLM | Corning |
| α-Naphthoflavone | Sigma-Aldrich |
| Ketoconazole | Sigma-Aldrich |
| Phenacetin | TOKYO CHEMICAL INDUSTRY CO., LTD. |
| Midazolam | Toronto Research Chemicals |
| Testosterone | Shanghai Xian Ding Biotechnology Co. Ltd. |
| Acetaminophen | Bide Pharmatech Co., Ltd. |
| 1'-Hydroxy Midazolam | Toronto Research Chemicals |
| 6β-hydroxy Testosterone | Cayman |
| Acetaminophen-$d_4$ | Toronto Research Chemicals |
| 1'-Hydroxy Midazolam-$^{13}C_3$ | Toronto Research Chemicals |
| 6β-Hydroxytestosterone-$d_7$ | Corning |
| nicotinamide adenine dinucleotide phosphate (NADP) | Sigma-Aldrich |
| Glucose 6-phosphate (G6P) | Shanghai yuanye Bio-Technology Co., Ltd. |
| Glucose-6-phosphate dehydrogenase (G6PDH) | Shanghai Quanyang Trading Co., Ltd. |
| Magnesium chloride ($MgCl_2$) | Shanghai Lingfeng Chemical Reagent Co., Ltd. |
| Potassium dihydrogen phosphate ($KH_2PO_4$) | Shanghai Lingfeng Chemical Reagent Co., Ltd. |
| Dipotassium phosphate trihydrate ($K_2HPO_4 \cdot 3H_2O$) | Shanghai Experimental Reagent Co., Ltd. |
| Dimethyl sulfoxide (DMSO) | J&K Scientific |
| Methanol (MeOH) | Merck Millipore |
| Acetonitrile (ACN) | Merck Millipore |
| Formic acid (FA) | Alfa Aesar |

Experimental Methods and Procedures:

The probe substrate, test compound, human liver microsomes, and cofactors were incubated together. The concentration of the metabolic product of the probe substrate was detected using LC-MS/MS to calculate the $IC_{50}$ values. In the vehicle control samples, the test compound was replaced with an equal volume of vehicle, and the enzyme activity of the vehicle control samples was set as 100%. The detailed information regarding the concentration of human liver microsomes, the concentration of the probe substrates for each CYP, the incubation time, positive controls, and the metabolic products used in the experiment are presented in the table below:

TABLE 20

| CYP | Probe substrate | Substrate concentration (μM) | Protein concentration (mg/mL) | Incubation Time (min) | Positive control Inhibitor | Metabolic product (Analyte) |
|---|---|---|---|---|---|---|
| 1A2 | Phenacetin | 75.0 | | 10 | α-Naphthoflavone | Acetaminophen |
| 3A | Midazolam | 2.00 | 0.100 | 3 | Ketoconazole | 1'-Hydroxy midazolam |
| 3A | Testosterone | 40.0 | | 10 | Ketoconazole | 6β-Hydroxytestosterone |

Incubation of Test Compounds and Positive Control Inhibitors:

All samples were incubated in a water bath at 37° C. Each concentration of the test compounds was prepared in triplicate, and each concentration of the positive control inhibitors was prepared in duplicate. The incubation system included a mixed working solution of the probe substrate (at specified concentrations) of the corresponding isozyme and microsomes (0.100 mg protein/mL), along with the working solution of the test compound or positive control inhibitor (at a series of final concentrations). All samples were preheated at 37° C. for 10 minutes. The reaction was initiated by adding cofactors to the preheated samples. For the CYP3A metabolic reaction using midazolam as the probe substrate, the reaction time was 3 minutes. For all other reactions, the reaction time was 10 minutes.

Vehicle Control Incubation:

Vehicle control data served as a baseline for calculating the activity of each isozyme in the incubation system. The vehicle control was categorized into two types: (1) the vehicle control for the test compound, conducted in triplicate, where the incubation system included a mixed working solution of the probe substrate of the corresponding isoenzyme (specified concentration) and microsomes (0.100 mg/mL), and the corresponding vehicle DMSO: methanol (v: v, 1:9); (2) the vehicle control for the positive control inhibitor, conducted in duplicate, where the incubation system included a mixed working solution of the probe substrate of the corresponding isoenzyme (specified concentration) and microsomes (0.100 mg protein/mL), and the corresponding vehicle methanol. All samples were preheated at 37° C. for 10 minutes. The reaction was initiated by adding cofactors to the preheated samples. For the CYP3A metabolic reaction using midazolam as the probe substrate, the reaction time was 3 minutes. For all other reactions, the reaction time was 10 minutes.

Sample Processing:

Upon reaching the respective reaction times for the incubation systems of the various isoenzymes, 200 μL of termination solution containing the appropriate internal standard was added to the reaction plate to terminate the reaction. The samples were thoroughly vortexed and then centrifuged at 3220×g for 20 minutes. The supernatant was then collected and diluted with a suitable diluent at a specific ratio. The reaction plate was placed on a shaker to ensure thorough mixing. The metabolites of the probe substrates were then analyzed using LC-MS/MS. If immediate analysis was not possible, the samples were stored at 2-8° C. for future use.

Post-incubation, the samples underwent protein precipitation and subsequent quantitative analysis of the probe substrate metabolites using LC-MS/MS.

Data Analysis:

The activity of various CYP isoenzymes was reflected by the production rate of metabolites from each probe substrate. The activity of each isoenzyme in the vehicle control incubation system, which did not contain the test compound or positive inhibitor, was set at 100%. The residual activity percentage of each isoenzyme was determined by comparing the metabolite production rate of the probe substrate in the presence of different concentrations of the test compound or positive inhibitor to that of the vehicle control samples, then multiplying by 100%. The residual activity percentage was plotted on the y-axis, and the inhibitor concentration on the x-axis. Non-linear regression analysis was performed using a three-parameter or four-parameter model in SigmaPlot (V.14) software to calculate the $IC_{50}$ values of the test compounds and positive inhibitors. If the $IC_{50}$ value obtained from the SigmaPlot fitting exceeded the highest administered concentration (100 μM) or if the $IC_{50}$ could not be determined, the $IC_{50}$ value was marked as ">100 μM".

Three-Parameter Equation:

$$y = \frac{\max}{1 + \left(\frac{x}{IC_{50}}\right)^{-hillslope}}$$

Four-Parameter Equation:

$$y = \min + \frac{\max - \min}{1 + \left(\frac{x}{IC_{50}}\right)^{-hillslope}}$$

max: Maximum enzyme activity.
min: Minimum enzyme activity.
x: Concentration of the test compound or positive control inhibitor.
y: Enzyme activity at the corresponding concentration.
Hillslope: Slope.
$IC_{50}$: Half-maximal inhibitory concentration.

The four-parameter equation was used when the minimum enzyme activity was within ±10%; otherwise, the three-parameter equation was used.

Experimental Results:

The $IC_{50}$ value of compound of formula (I) for CYP1A2 was 97.2 μM, for CYP3A (using midazolam as the substrate) was 8.38 μM, and for CYP3A (using testosterone as the substrate) was 10.9 μM. The compounds of the present disclosure exhibit weak inhibition on CYP enzymes, indicating a low risk of drug-drug interactions.

(2) Pharmacokinetic Study in Mice

Objective: To determine the concentration of the test compound in plasma at various time points after intravenous and intragastric administration in female Balb/c mice using the LC/MS/MS method. To investigate the pharmacokinetic behavior of the crystal form C of the compound of formula (I) in mice and to evaluate its pharmacokinetic characteristics.

Experimental Scheme:

Test animals: The animals were purchased from Shanghai Lingchang Biotechnology Co., Ltd.

Drug Preparation:

An appropriate amount of the sample was weighed and prepared into a 1 mg/ml solution, stirred and sonicated until a clear solution was obtained, with 15% HP-β-CD as the vehicle.

Administration: After an overnight fast, the IV group received intravenous administration at a dose of 5 mg/kg; the PO group received intragastric administration at a dose of 10 mg/kg.

Experimental Operation:

For the intravenous injection group, female Balb/c mice were administered the test compound, and blood samples (30 μL) were collected from the saphenous vein at 0.0833, 0.25, 0.5, 1, 2, 4, 8, and 24 hours post-administration. The samples were placed into commercially available anticoagulant tubes pre-filled with EDTA-K2. For the intragastric administration group, after administering the test compound, blood samples (30 μL) were collected from the jugular vein at 0.25, 0.5, 1, 2, 4, 8, 12, and 24 hours. These samples were also placed into commercially available anticoagulant tubes pre-filled with EDTA-K2. Following centrifugation (3,200 g, 4° C., 10 minutes), the plasma was transferred to pre-chilled centrifuge tubes, flash-frozen in dry ice, and stored in an ultra-low temperature freezer at −60° C. or lower until LC-MS/MS analysis. Animals were allowed to eat 4 hours post-dosing. The concentration of the test compound in the plasma of mice after intravenous and intragastric administration was determined using the LC/MS/MS method. The method had a linear range of 2.00 to 2000 nM.

Experimental Results:

TABLE 21

| Pharmacokinetic parameters of mice | | | | | |
|---|---|---|---|---|---|
| Route of administration | $C_{max}$ (nM) | $T_{1/2}$ (h) | $Vd_{ss}$ (L/kg) | Cl (mL/min/kg) | $AUC_{0-last}$ (nM · h) | F (%) |
| IV, 5 mg/kg | / | 5.16 | 11.1 | 30.2 | 5270 | / |
| PO, 10 mg/kg | 779 | 4.72 | / | / | 5856 | 55.4 |

The crystal form C of the compound of formula (I) exhibits metabolic stability, extensive tissue distribution, and high oral bioavailability in mice, indicating relatively good pharmacokinetic characteristics in vivo.

(3) Pharmacokinetic Study in Rats

Objective: To determine the concentration of the test compound in plasma at various time points after intravenous and intragastric administration in male and female Sprague-Dawley rats using the LC/MS/MS method. To investigate the pharmacokinetic behavior of the crystal form B of the compound of formula (II) in rats and to evaluate its pharmacokinetic characteristics.

Experimental Scheme:

Test Animals: The animals were purchased from Beijing Vital River Laboratory Animal Technology Co., Ltd.

Drug Preparation:

An appropriate amount of the sample was weighed and prepared into a 0.2 mg/ml solution, and stirred until a clear solution was obtained, with 20% SBE-β-CD as the vehicle.

Administration: After an overnight fast, the IV group received intravenous administration at a dose of 1 mg/kg; the PO group received intragastric administration at a dose of 2 mg/kg.

Experimental Operation:

For the intravenous injection group, male and female Sprague-Dawley rats were administered the test compound, and blood samples (200 μL) were collected from the jugular vein at 0.0830, 0.250, 0.500, 1.00, 2.00, 4.00, 6.00, 8.00, 24.0, 32.0, and 48.0 hours post-administration. The samples were placed into commercially available anticoagulant tubes pre-filled with EDTA-K2. For the intragastric administration group, after administering the test compound, blood samples (200 μL) were collected from the jugular vein at 0.250, 0.500, 1.00, 2.00, 4.00, 6.00, 8.00, 24.0, 32.0, and 48.0 hours. These samples were also placed into commercially available anticoagulant tubes pre-filled with EDTA-K2. Following centrifugation (3,200 g, 4° C., 10 minutes), the plasma was transferred to pre-chilled centrifuge tubes, flash-frozen in dry ice, and stored in an ultra-low temperature freezer at −60° C. or lower until LC-MS/MS analysis. Animals were allowed to eat 4 hours post-dosing. The concentration of the test compound in the plasma of rats after intravenous and intragastric administration was determined using the LC/MS/MS method. The method had a linear range of 2.00 to 2000 nM.

Experimental Results:

TABLE 22

| Pharmacokinetic parameters of rats | | | | | | |
|---|---|---|---|---|---|---|
| Route of administration | $C_{max}$ (nM) | $T_{1/2}$ (h) | $Vd_{ss}$ (L/kg) | Cl (mL/min/kg) | $AUC_{0-last}$ (nM · h) | F (%) |
| IV, 1 mg/kg | / | 10.6 | 13.6 | 22.1 | 1710 | / |
| PO, 2 mg/kg | 87.7 | 10.3 | / | / | 1630 | 47.7 |

The crystal form B of the compound of formula (II) exhibits metabolic stability, extensive tissue distribution, and high oral bioavailability in rats, indicating relatively good pharmacokinetic characteristics in vivo.

(4) Pharmacokinetic Study in Beagle Dogs

Objective: To determine the concentration of the test compound in plasma at various time points after intravenous and intragastric administration in male and female Beagle dogs using the LC/MS/MS method. To investigate the pharmacokinetic behavior of the crystal form B of the compound of formula (II) in Beagle dogs and to evaluate its pharmacokinetic characteristics.

Experimental Scheme:

Test animals: The animals were purchased from Beijing Marshall Biotechnology Co., Ltd.

Drug Preparation:

An appropriate amount of the sample was weighed and prepared into 0.2 mg/mL and 0.3 mg/mL solutions, stirred until a clear solution was obtained, with 20% SBE-β-CD as the vehicle.

Administration: After an overnight fast, the IV group received intravenous administration at a dose of 0.3 mg/kg; the PO group received intragastric administration at a dose of 1 mg/kg.

Experimental Operation:

For the intravenous injection group, Beagle dogs were administered the test compound, and blood samples (800 μL) were collected from the peripheral vein at 0.25, 0.5, 1, 2, 4, 6, 8, 24, 32, 48, 72, and 96 hours post-administration. The samples were placed into commercially available anticoagulant tubes pre-filled with EDTA-K2. For the intragastric administration group, after administering the test compound, blood samples (800 μL) were collected from the peripheral vein at 0.25, 0.5, 1, 2, 4, 6, 8, 24, 32, 48, 72, and 96 hours. These samples were also placed into commercially available anticoagulant tubes pre-filled with EDTA-K$_2$. Following centrifugation (3,200 g, 2-8° C., 10 minutes), the plasma was transferred to pre-chilled centrifuge tubes, flash-frozen in dry ice, and stored in an ultra-low temperature freezer at −60° C. or lower until LC-MS/MS analysis. Animals were allowed to eat 4 hours post-dosing. The concentration of the test compound in the plasma of Beagle dogs after intravenous and intragastric administration was determined using the LC/MS/MS method. The method had a linear range of 2.00 to 2000 nM.

Experimental Results:

TABLE 23

Pharmacokinetic parameters in Beagles

| Route of administration | $C_{max}$ (nM) | $T_{1/2}$ (h) | $Vd_{ss}$ (L/kg) | Cl (mL/min/kg) | $AUC_{0\text{-}last}$ (nM·h) | F (%) |
|---|---|---|---|---|---|---|
| IV, 0.3 mg/kg | / | 24.2 | 7.48 | 3.80 | 1310 | / |
| PO, 1 mg/kg | 61.0 | 21.6 | / | / | 2270 | 52.0 |

The crystal form B of the compound of formula (II) according to the present disclosure exhibits metabolic stability, extensive tissue distribution, and high oral bioavailability in Beagle dogs, indicating relatively good pharmacokinetic characteristics in vivo.

Experimental Example 3: In Vivo Pharmacodynamic Evaluation (1) In Vivo Pharmacodynamic Study of Breast Cancer MCF-7 Cell Subcutaneous Xenograft Tumor BALB/c Nude Mouse Model Objective: This study aimed to evaluate the in vivo efficacy of the crystal form C of the compound of formula (I) using a human breast cancer MCF-7 cell subcutaneous xenograft tumor model in nude mice.

Experimental Materials:

TABLE 24

| Name | Manufacturer |
|---|---|
| EMEM medium | ATCC |
| Trypsin | Gibco |
| Matrigel | CORNING |
| Anti-anti | Gibco |
| Fetal bovine serum | Cellmax |

Experimental Methods and Procedures:

Cell Culture Preparation:

Human breast cancer MCF-7 cells were routinely cultured in vitro as a monolayer under the following conditions: EMEM medium (EBSS; ATCC) supplemented with 10% fetal bovine serum (Cellmax), 2 mM glutamine (Gibco), and 1% non-essential amino acids (NEAA; Gibco), in a 37° C., 5% $CO_2$ incubator. Routine digestion with trypsin-EDTA (Gibco) was performed twice a week for passaging. When the cell saturation density was 80% to 90% and the number of cells reached the required level, the cells were collected, counted, and inoculated.

Test Animals: The animals were purchased from Beijing Vital River Laboratory Animal Technology Co., Ltd. (Zhejiang branch).

Tumor Cell Inoculation and Grouping

Cell inoculation: Estrogen pellets (0.36 mg/pellet; IRA) were subcutaneously inoculated into the left dorsum of each mouse. Three days later, 0.2 mL (1×10$^7$ cells) of MCF-7 cells (mixed with Matrigel; CORNING, volume ratio 1:1) were subcutaneously inoculated into the right dorsum of each mouse. When the average tumor volume reached 188 mm$^3$, the mice were grouped and the administration of compounds began.

TABLE 25

Grouping and administration regimen of experimental animals

| Group | Compound | Dose (mg/kg) | Route of administration | Frequency of administration |
|---|---|---|---|---|
| 1 | blank control | — | PO | QD |
| 2 | Fulvestrant | 5 mg/mouse | SC | QW |
| 3 | Palbociclib | 25 | PO | QD |
| 4 | Compound of formula (I) | 1 | PO | QD |
| 5 | Compound of formula (I) | 3 | PO | QD |
| 6 | Compound of formula (I) | 10 | PO | QD |
| 7 | Compound of formula (I) | 30 | PO | QD |
| 8 | Compound of formula (I) + Palbociclib | 3 + +25 | PO | QD |

Drug Preparation:

An appropriate amount of the compound of formula (I) was weighed and prepared into 0.1, 0.3, 1, and 3 mg/mL solutions. These were vortexed briefly and then sonicated until a clear solution was obtained, with 10% HP-β-CD as the vehicle. An appropriate amount of Palbociclib was weighed and prepared into a 2.5 mg/mL solution. The pH was adjusted to 4.0, vortexed briefly, and then sonicated until a clear solution was obtained. The vehicle was 50 mM sodium lactate buffer. Fulvestrant was used as the commercially available injection Faslodex.

Tumor Measurement and Experimental Indicators:

Tumor diameters were measured twice a week with a vernier caliper. The formula for calculating tumor volume was: $V=0.5a\times b^2$, wherein a and b represented the long and short diameters of the tumor, respectively.

The antitumor efficacy of the compounds was evaluated using Tumor Growth Inhibition (TGI, %) and relative tumor proliferation rate (T/C, %). Relative tumor proliferation rate (T/C, %)=$T_{RTV}/C_{RTV}\times 100\%$ ($T_{RTV}$: the mean RTV of the treatment group; $C_{RTV}$: the mean RTV of the control group). RTV was calculated based on the tumor measurement results, the formula for calculation is RTV=$V_t/V_0$, where $V_0$ was the tumor volume at the time of grouping and administration (D0), and $V_t$ was the tumor volume at a specific measurement time. $T_{RTV}$ and $C_{RTV}$ were taken from the same day's data.

TGI (%) reflected the tumor growth inhibition rate. TGI (%)=[1−(average tumor volume at the end of administration in a treatment group−average tumor volume at the beginning of administration in this treatment group)/(average tumor volume at the end of treatment in the control group−average tumor volume at the beginning of treatment in the control group)]×100%.

The Q value of combined medication index was calculated using the Jin formula. The criteria for judgment were as follows: a Q value of 0.85 to 1.15 indicated synergistic addition (+); a Q value>1.15 to 2.0 indicated enhancement (++); a Q value<0.85 to 0.55 indicated antagonism (−); and a Q value<0.55 indicated significant antagonism (−−). The formula was Q=Ea+b/(Ea+Eb−Ea×Eb), where Ea+b was the tumor inhibition rate of the combined medication group, and Ea and Eb were the tumor inhibition rates of the single medication groups, respectively.

At the end of the experiment, tumor weight would be measured, and the T/C$_{weight}$ percentage would be calculated, where T$_{weight}$ and C$_{weight}$ represented the tumor weights of the medication group and the vehicle control group, respectively.

Statistical analysis was performed using SPSS software based on RTV data at the end of the experiment. Inter-group comparisons were analyzed using one-way ANOVA. If the variance was unequal (F value showed significant difference), the Games-Howell method was applied for testing. A p value<0.05 was considered to indicate a significant difference.

Figure 10:
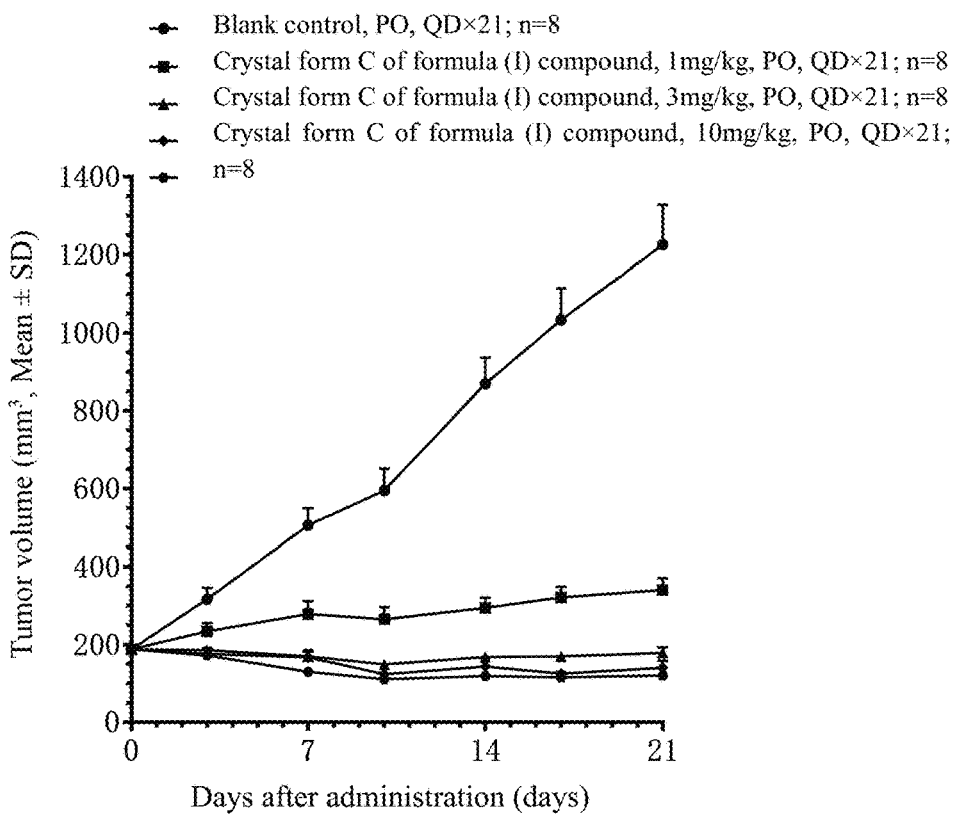
FIG. 10 shows tumor growth curves in the subcutaneous xenograft model of human breast cancer MCF7 cells in tumor-bearing mice after administration of the test compound (crystal form C of the compound of formula (I)).
Figure 11:
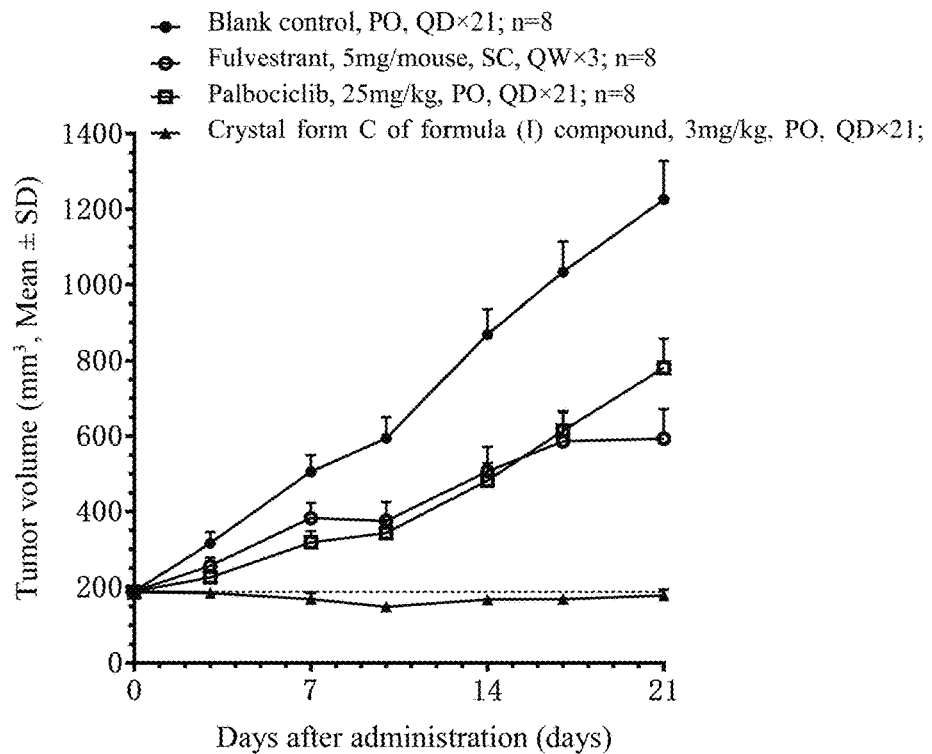
FIG. 11 shows tumor growth curves in the subcutaneous xenograft model of human breast cancer MCF7 cells in tumor-bearing mice after administration of the test compound (crystal form C of the compound of formula (I), as compared to fulvestrant and palbociclib).

Experimental Results:

This experiment evaluated the efficacy of the crystal form C of the compound of formula (I) in a human breast cancer xenograft model, using a vehicle control group as a reference. The tumor volumes at different time points and the corresponding statistical analysis results are shown in Table 14 and FIG. 10. The changes in body weight of the mice during the administration period are shown in FIG. 11.

On the 21st day after administration, the average tumor volume of the blank control group was 1225 mm$^3$. The average tumor volumes of compound (I) at doses of 1 mg/kg, 3 mg/kg, 10 mg/kg, and 30 mg/kg were 340 mm$^3$, 179 mm$^3$, 140 mm$^3$, and 121 mm$^3$, respectively. The T/C values were 27.2%, 14.8%, 11.3%, and 9.7%, and the TGI values were 85.3%, 100.9%, 104.6%, and 106.5%, respectively. Compared to the control group, the p-values were 0.003, 0.001, 0.001, and 0.001, respectively. At doses of 10 mg/kg and 30 mg/kg, the objective response rate (ORR) reached 25%. Therefore, the crystal form C of the compound of formula (I) demonstrated significant tumor inhibitory effects at the above doses, showing a dose-response relationship as the dose increased.

TABLE 26

Tumor inhibition effects of test compounds on subcutaneous xenograft model of breast cancer MCF7 cells

| Group | Tumor volume (mm$^3$) (Day 0) | Tumor volume (mm$^3$)$^a$ (Day 21) | RTV (Day 21) | T/C (%) | TGI (%) | DCR % | ORR % |
|---|---|---|---|---|---|---|---|
| blank control | 188 ± 12 | 1225 ± 103 | 6.66 ± 0.70 | — | — | — | — |
| Fulvestrant 5 mg/mouse, QW | 188 ± 12 | 593 ± 79 | 3.12 ± 0.31 | 46.9 | 60.9 | 0 | — |
| Palbociclib 25 mg/kg, QD | 188 ± 12 | 781 ± 77 | 4.26 ± 0.51 | 64.0 | 42.8 | 12.5 | 0 |
| Crystal form C of the compound of formula (I), 1 mg/kg, QD | 188 ± 12 | 340 ± 30 | 1.82 ± 0.12 | 27.2 | 85.3 | — | 0 |
| Crystal form C of the compound of formula (I), 3 mg/kg, QD | 188 ± 13 | 179 ± 14 | 0.99 ± 0.11 | 14.8 | 100.9 | 100 | 0 |
| Crystal form C of the compound of formula (I), 10 mg/kg, QD | 188 ± 12 | 140 ± 18 | 0.75 ± 0.09 | 11.3 | 104.6 | — | 25 |
| Crystal form C of the compound of formula (I), 30 mg/kg, QD | 188 ± 12 | 121 ± 13 | 0.64 ± 0.07 | 9.7 | 106.5 | — | 25 |
| Crystal form C of the compound of formula (I), 3 mg/kg + Palbociclib | 188 ± 12 | 79 ± 14 | 0.41 ± 0.04 | 6.1 | 110.5 | — | 87.5 |

On day 21, the average tumor volumes for the fulvestrant (5 mg/mouse) and palbociclib (25 mg/kg) single drug groups were 593 mm$^3$ and 781 mm$^3$, respectively. The T/C values were 46.9% and 64.0%, and the TGI values were 60.9% and 42.8%, with p-values of 0.019 and 0.219, respectively, compared to the control group. Therefore, the single drug of fulvestrant exhibited antitumor activity, while the single drug of palbociclib did not show antitumor activity. Compared to these reference compounds, the crystal form C of the compound of formula (I) at 3 mg/kg exhibited stronger antitumor activity, with a disease control rate (DCR) of 100%.

The single drug of palbociclib did not show antitumor activity; however, when compound (I) (3 mg/kg) was combined with palbociclib, the average tumor volume was 79 mm$^3$, the T/C value was 6.1%, and the TGI was 110.5%. Compared to the control group, palbociclib, and the crystal form C of the compound of formula (I) (3 mg/kg) groups, the p-values were 0.001, 0.002, and 0.012, respectively. The objective response rate (ORR) was 87.5%. The Q value calculated using the Jin formula was 1.10 (+), indicating that the combined medication showed stronger antitumor activity than the single drug of crystal form C of the compound of formula (I), demonstrating a synergistic additive effect.

Experimental conclusion:

Compared to the blank control group, the crystal form C of the compound of formula (I) exhibited significant tumor inhibitory effects at doses of 1 mg/kg, 3 mg/kg, 10 mg/kg, and 30 mg/kg, with an effective dose starting at 1 mg/kg (TGI of 85.3%). When the crystal form C of the compound of formula (I) (3 mg/kg) was combined with palbociclib, it demonstrated stronger antitumor activity than single drug. The tumor-bearing mice tolerated the crystal form C of the compound of formula (I) well. The compounds of the present disclosure demonstrated excellent tumor inhibition efficacy in the mouse efficacy model, showing good potential for clinical treatment.

(2) In Vivo Pharmacodynamic Study of Human Breast Cancer MCF-7 Cells with ESR1 D538G Mutation Subcutaneous Xenograft Tumor Mouse Model Objective of the experiment: The purpose of this study is to evaluate the in vivo antitumor effects of the crystal form B of the compound of formula (II) using a subcutaneous xenograft tumor model constructed with human breast cancer MCF-7 cells carrying the ESR1 D538G mutation in BALB/c Nude mice.

TABLE 27

| Name | Manufacturer |
| --- | --- |
| Fetal bovine serum | Dongling Biotechnology |
| EMEM | ATCC |
| PBS | Hyclone |
| EDTA | gibco |
| L-Glutamine | gibco |
| NEAA | gibco |
| Matrigel | Corning |
| Anti-anti | gibco |

Experimental Methods and Procedures:
Cell Culture Preparation:

Human breast cancer MCF-7 cells carrying the ESR1 D538G mutation were routinely cultured in vitro as a monolayer. The culture conditions included EMEM medium supplemented with 10% fetal bovine serum, 1% Antibiotic-Antimycotic, 2 mM L-Glutamine, and 1% NEAA, incubated at 37° C. in a 5% $CO_2$ incubator. Routine digestion with trypsin-EDTA was performed twice a week for passaging. When the cell saturation density was 80% to 90% and the number of cells reached the required level, the cells were collected, counted, and inoculated.

Test animals: The animals were purchased from Beijing Vital River Laboratory Animal Technology Co., Ltd.
Tumor Cell Inoculation and Grouping Cell inoculation: Each mouse was subcutaneously inoculated with 0.2 mL ($10 \times 10^6$) MCF-7 ESR1 D538G cells (PBS+Matrigel, volume ratio 1:1) on the right rear back. When the average tumor volume reached 147 $mm^3$, the mice were grouped for treatment. Experimental groups and treatment regimens are presented in the following table. The first day of administration was designated as day 0.

TABLE 28

Grouping and administration regimen of experimental animals

| Group | Compound | Dose (mg/kg) | Route of administration | Frequency of administration |
| --- | --- | --- | --- | --- |
| 1 | Blank control | — | PO | QD |
| 2 | Palbociclib | 50 | PO | QD |
| 3 | Crystal form B of the compound of formula (II) | 5 | PO | QD |
| 4 | Crystal form B of the compound of formula (II) | 15 | PO | QD |
| 5 | Crystal form B of the compound of formula (II) | 50 | PC | QD |
| 6 | Crystal form B of the compound of formula (II) + Palbociclib | 5 + 50 | PO | QD |

Drug Preparation:

An appropriate amount of the crystal form B of the compound of formula (II) was weighed and prepared into 0.5, 1.5, and 5.0 mg/mL solutions. These were vortexed briefly and then sonicated until a clear solution was obtained, with 10% HP-β-CD as the vehicle. An appropriate amount of Palbociclib was weighed and prepared into a 5 mg/mL solution. The pH was adjusted to 4.0, vortexed briefly, and then sonicated until a clear solution was obtained. The vehicle was 50 mM sodium lactate buffer.
Tumor Measurement and Experimental Indicators:

Tumor diameters were measured twice a week with a vernier caliper. The formula for calculating tumor volume was: $V=0.5a \times b^2$, wherein a and b represented the long and short diameters of the tumor, respectively.

The antitumor efficacy of the compound was evaluated using TGI (%) or relative tumor proliferation rate T/C (%). Relative tumor proliferation rate (T/C, %)=$T_{RTV}/C_{RTV} \times 100\%$ ($T_{RTV}$: the mean RTV of the treatment group; $C_{RTV}$: the mean RTV of the negative control group). RTV was calculated based on the tumor measurement results, the formula for calculation is RTV=$V_t/V_0$, where $V_0$ is the tumor volume at the time of grouping and administration (D0), and $V_t$ is the tumor volume at a specific measurement time. $T_{RTV}$ and $C_{RTV}$ were taken from the same day's data.

TGI (%) reflected the tumor growth inhibition rate. TGI (%)=[1−(average tumor volume at the end of administration in a treatment group−average tumor volume at the beginning of administration in this treatment group)/(average tumor volume at the end of treatment in the vehicle control group−average tumor volume at the beginning of treatment in the vehicle control group)]×100%.

At the end of the experiment, tumor weight would be measured, and the T/$C_{weight}$ percentage would be calculated, where $T_{weight}$ and $C_{weight}$ represented the tumor weights of the medication group and the vehicle control group, respectively.

Figure 12:
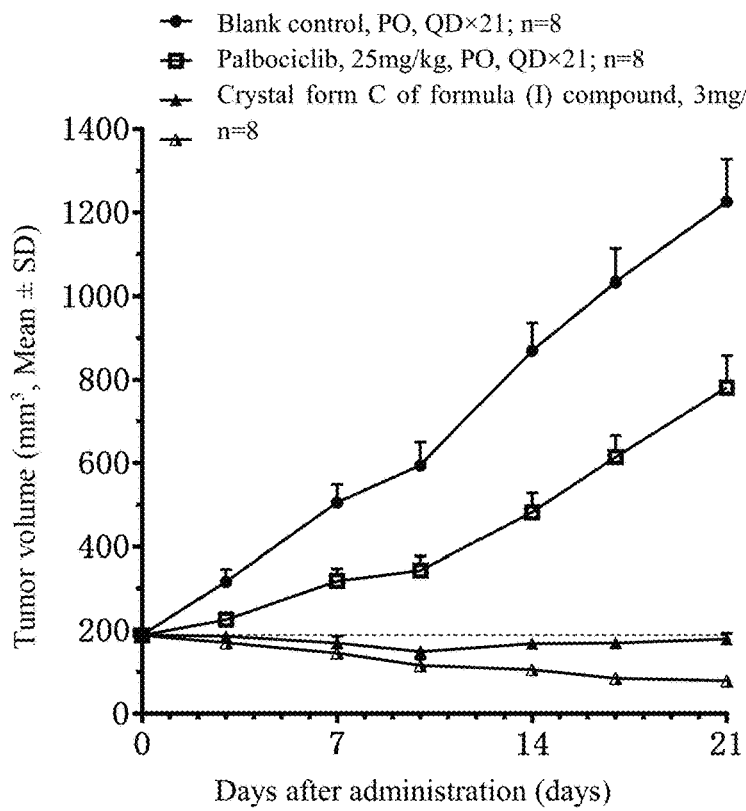
FIG. 12 shows tumor growth curves in the subcutaneous xenograft model of human breast cancer MCF7 cells in tumor-bearing mice after administration of the test compound (crystal form C of the compound of formula (I) in combination with palbociclib).
Figure 13:
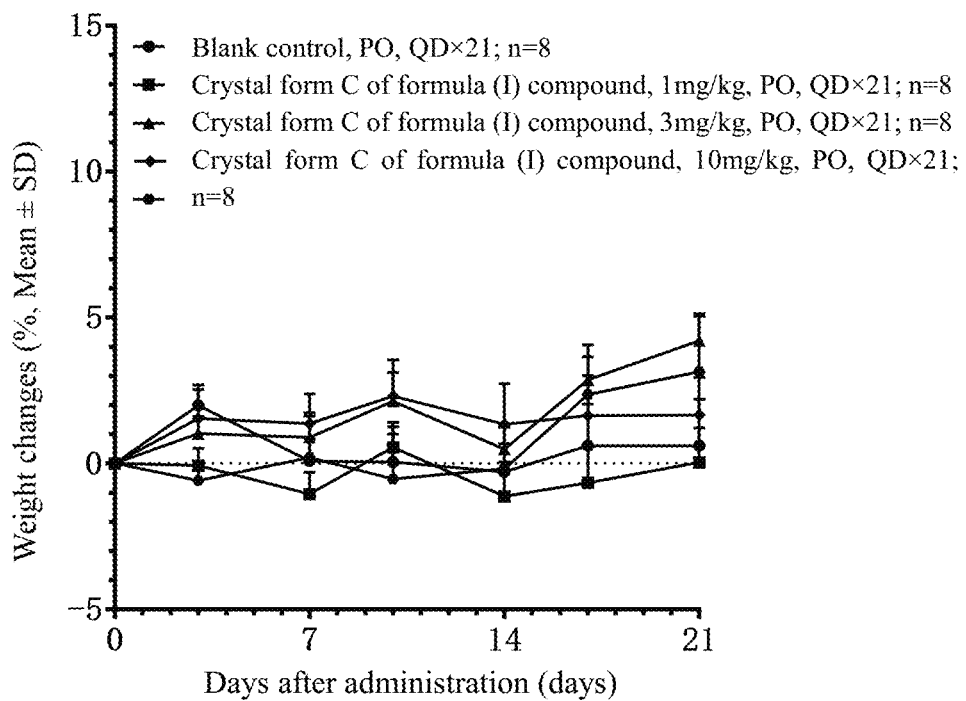
FIG. 13 shows percentage (%) changes in body weight during the administration of crystal form C of the compound of formula (I) in the subcutaneous xenograft model of human breast cancer MCF7 cells in tumor-bearing mice.
Figure 14:
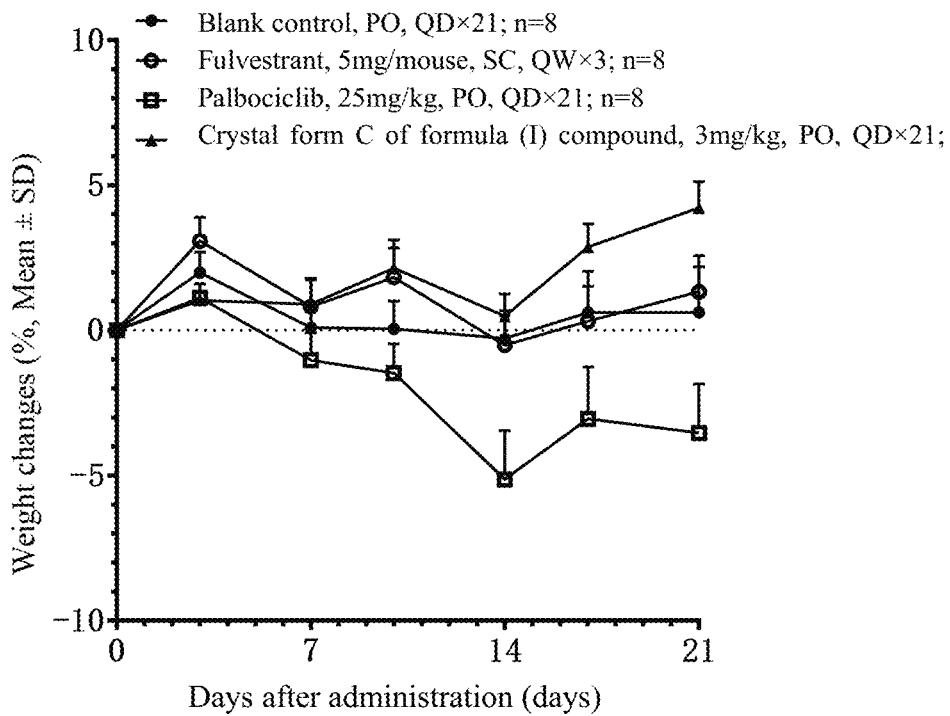
FIG. 14 shows percentage (%) changes in body weight during the administration of crystal form C of the compound of formula (I), as compared to fulvestrant and palbociclib, in FIG. 15 shows percentage (%) changes in body weight during the administration of crystal form C of the compound of formula (I) combined with palbociclib in the subcutaneous xenograft model of human breast cancer MCF7 cells in tumor-bearing mice.
Figure 15:
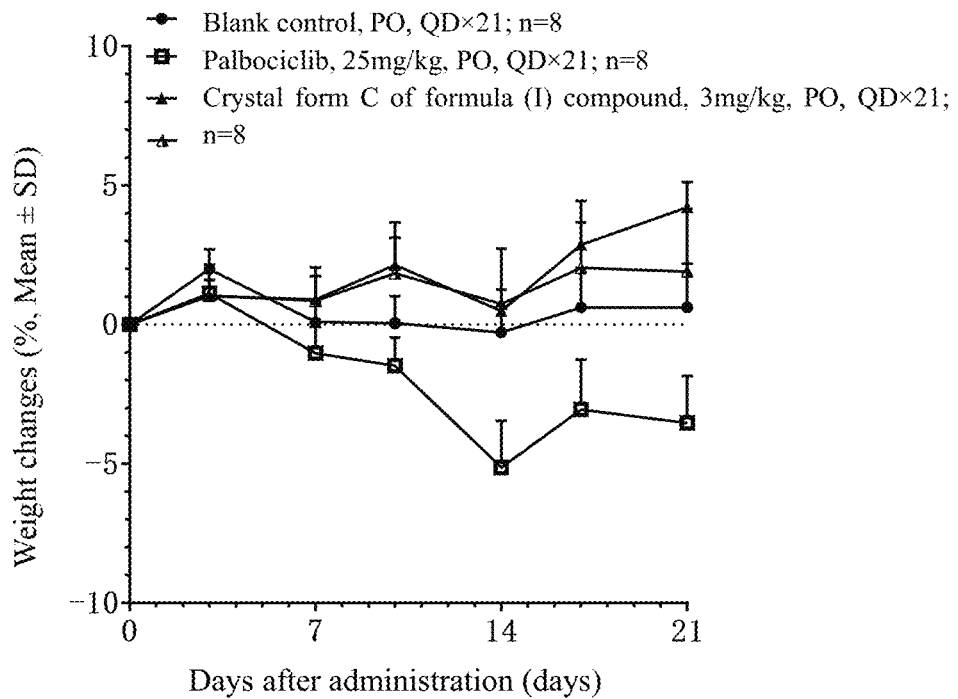
Figure 16:
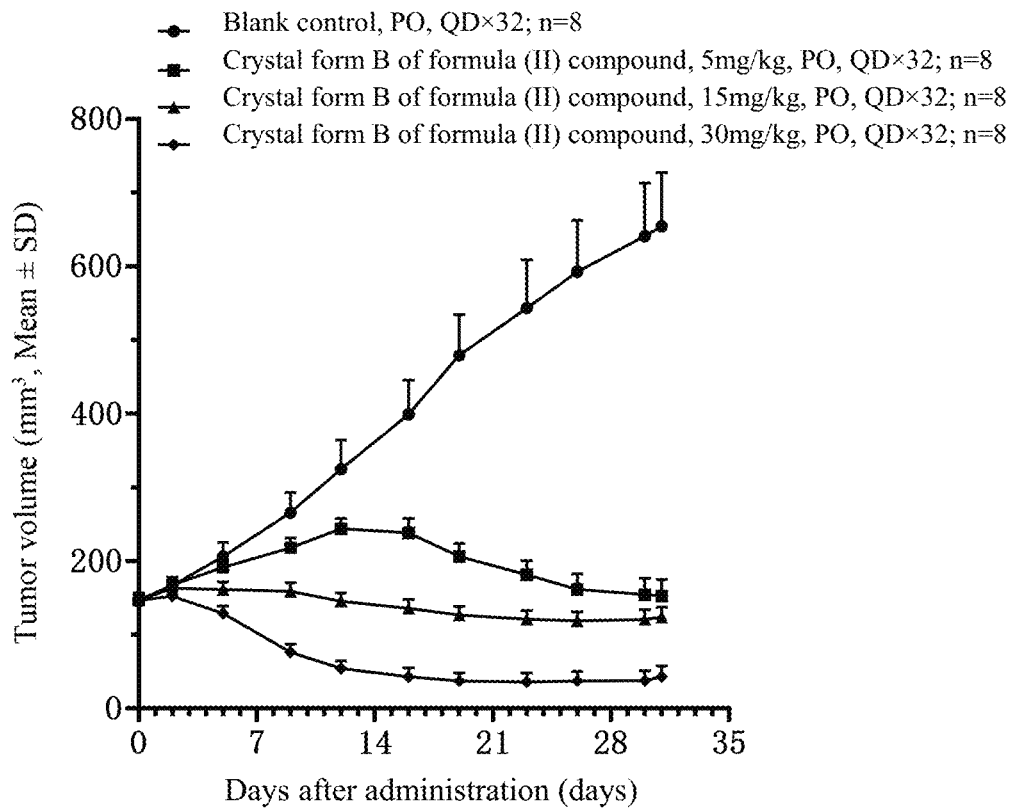
FIG. 16 shows tumor growth curves of crystal form B of the compound of formula (II) in the subcutaneous xenograft model of MCF7 cells carrying the ESR1 D538G mutation in tumor-bearing mice.
Figure 17:
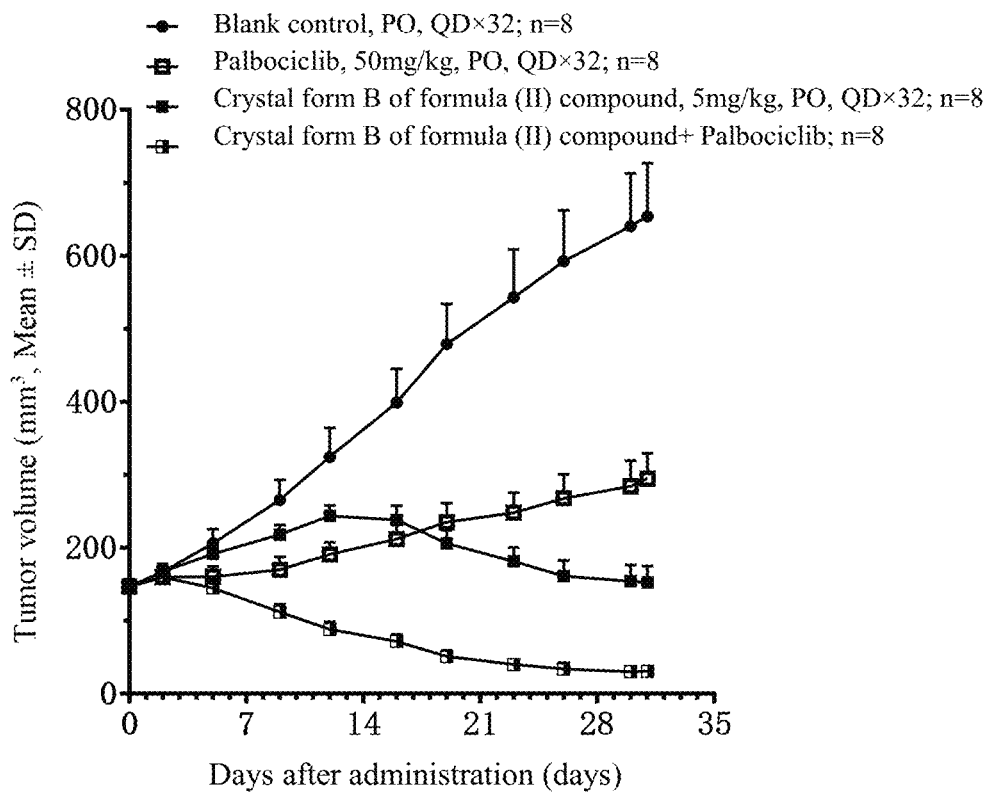
FIG. 17 shows tumor growth curves of crystal form B of the compound of formula (II) combined with palbociclib in the subcutaneous xenograft model of MCF7 cells carrying the ESR1 D538G mutation in tumor-bearing mice.
Figure 18:
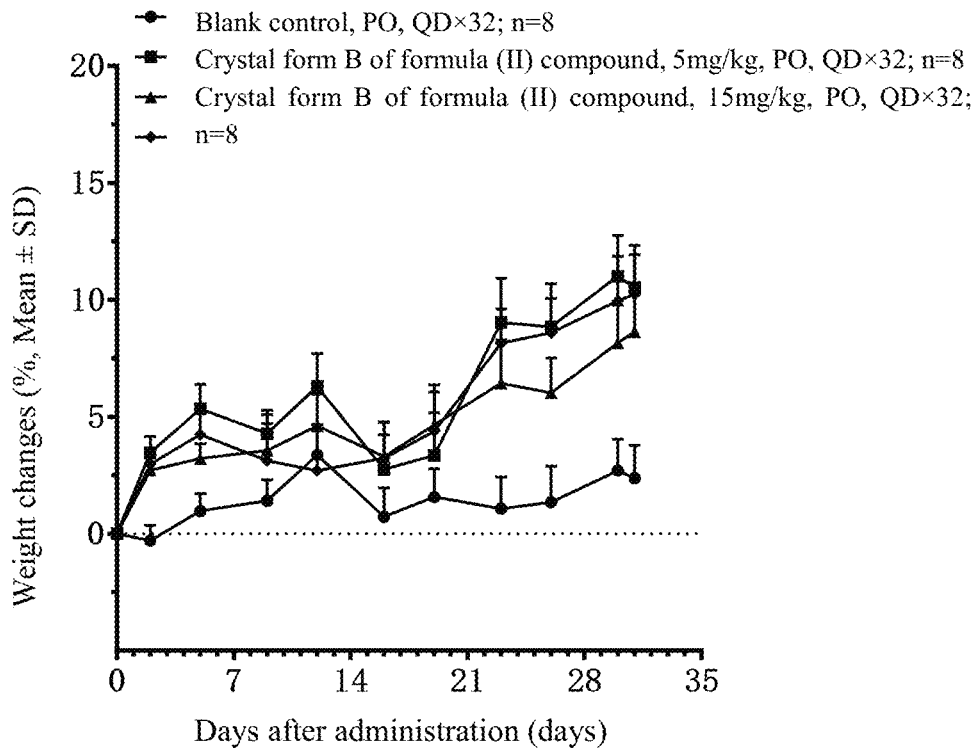
FIG. 18 shows percentage (%) changes in body weight during the administration of crystal form B of the compound of formula (II) in the subcutaneous xenograft model of MCF7 cells carrying the ESR1 D538G mutation in tumor-bearing mice.
Figure 19:
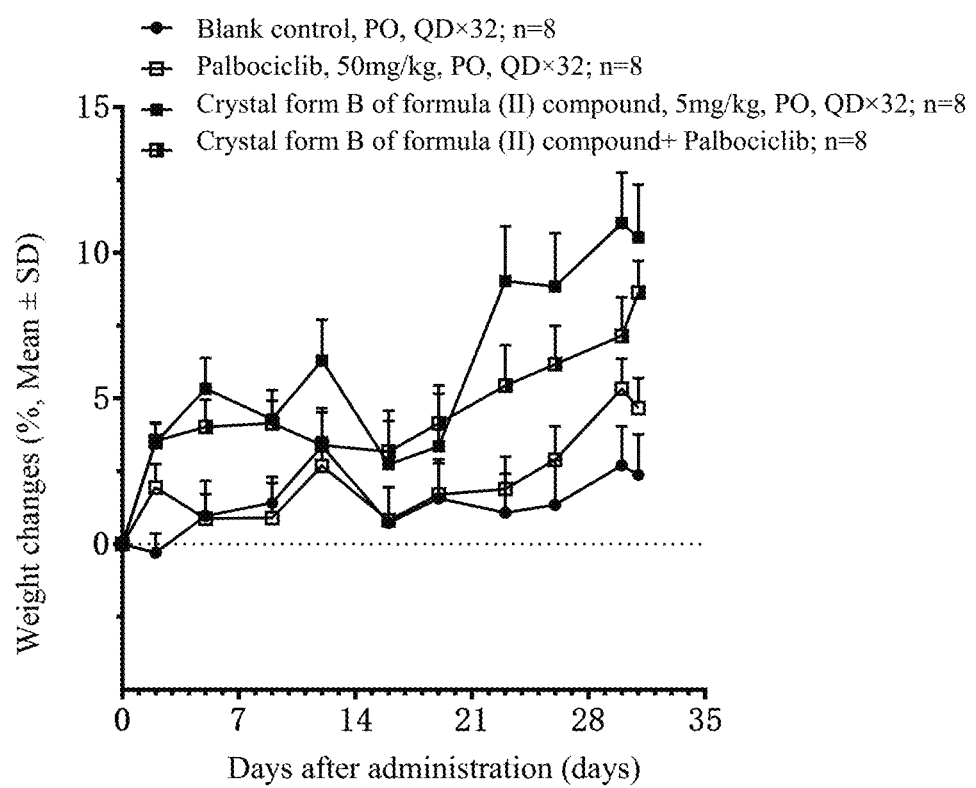
FIG. 19 shows percentage (%) changes in body weight during the administration of crystal form B of the compound of formula (II) combined with palbociclib in the subcutaneous xenograft model of MCF7 cells carrying the ESR1 D538G mutation in tumor-bearing mice.

Statistical analysis was performed on the RTV data at the end of the experiment using GraphPad Prism software. One-way ANOVA was used for comparisons among multiple groups, with a p-value<0.05 indicating significant differences and a p-value>0.05 indicating no significant differences.
Experimental Results:

The efficacy of the crystal form B of the compound of formula (II) was evaluated in a human breast cancer MCF7 cell carrying the ESR1 D538G mutation xenograft tumor model, with a blank control group as a reference. The tumor volumes at different time points for each group and their statistical analysis are presented in FIG. 12 and Table 29, respectively. The changes in body weight of the mice during the administration period are shown in FIG. 13.

TABLE 29

Antitumor efficacy of the test compound in the subcutaneous
xenograft tumor model of human breast cancer MCF7 ESR1 D538G cells

| Group | Tumor volume (mm³) (Day 0) | Tumor volume (mm³) (Day 31) | RTV (Day 31) | T/C (%) | TGI (%) | p value (One-way ANOVA) | ORR % |
|---|---|---|---|---|---|---|---|
| Blank control | 147 ± 9 | 654 ± 73 | 4.42 | — | — | — | — |
| Palbociclib, 50 mg/kg | 147 ± 10 | 295 ± 35 | 2.01 | 45.47 | 70.91 | <0.0001 | 0 |
| Crystal form B of the compound of formula (II), 5 mg/kg | 147 ± 9 | 153 ± 22 | 1.07 | 24.15 | 98.86 | <0.0001 | 0 |
| Crystal form B of the compound of formula (II), 15 mg/kg | 147 ± 10 | 124 ± 14 | 0.84 | 18.93 | 104.52 | <0.0001 | 14 |
| Crystal form B of the compound of formula (II), 50 mg/kg | 147 ± 7 | 43 ± 15 | 0.28 | 6.37 | 120.51 | <0.0001 | 100 |
| Crystal form B of the compound of formula (II) + Palbociclib, 5 + 50 mg/kg | 147 ± 10 | 31 ± 8 | 0.21 | 4.67 | 122.83 | <0.0001 | 100 |

On day 31 post-grouping, the mean tumor volume of the blank control group was 654 mm³. The mean tumor volume of the palbociclib (50 mg/kg) single drug group was 295 mm³, with a T/C value of 45.47% and a TGI of 70.91%, a p value<0.0001 compared to the blank control group, showing a significant antitumor effect (. For the crystal form B of the compound of formula (II), at doses of 5 mg/kg, 15 mg/kg, and 50 mg/kg, the mean tumor volumes were 153 mm³, 124 mm³, and 43 mm³, respectively. The corresponding T/C values were 24.15%, 18.93%, and 6.37%, and the TGI values were 98.86%, 104.52%, and 120.51%. All p-values compared to the blank control group were <0.0001. The crystal form B of the compound of formula (II) demonstrated significant antitumor effects at the aforementioned doses, with the objective response rate showing a favorable dose-dependence. In the combined medication group of the crystal form B of the compound of formula (II) (5 mg/kg) and palbociclib (50 mg/kg), the average tumor volume was 31 mm³, with a T/C of 4.67% and a TGI value of 122.83%. The p-value compared to the blank control group was <0.0001, and it was also statistically significant compared to the single drug groups of the crystal form B of the compound of formula (II) or palbociclib (p-value<0.0001, synergy factor of 2.21). The objective response rate in the combined medication group reached 100%. Therefore, the combined medication exhibited a more significant antitumor effect than single drug.

The above results suggested that the single drug of crystal form B of the compound of formula (II) had significant antitumor activity at doses of 5 mg/kg, 15 mg/kg, and 50 mg/kg in the human breast cancer MCF7 cells carrying the ESR1 D538G mutation subcutaneous xenografted tumor BALB/c nude mouse model. Additionally, at a dose of 5 mg/kg, the crystal form B of the compound of formula (II) demonstrated synergistic antitumor effects when combined with palbociclib (50 mg/kg), comparable to the antitumor activity of the crystal form B of the compound of formula (II) at a dose of 50 mg/kg.

Experimental Conclusion:

The crystal form B of the compound of formula (II) exhibited antitumor activity against the growth of subcutaneous xenograft tumors in MCF7 mice carrying the ESR1 D538G mutation, with a certain degree of dose dependence. When used in combination with palbociclib, the crystal form B of the compound of formula (II) shows superior in vivo antitumor effects compared to single drug. Throughout the experimental process, all groups of mice displayed good tolerability.

What is claimed is:

1. A compound of formula (III)

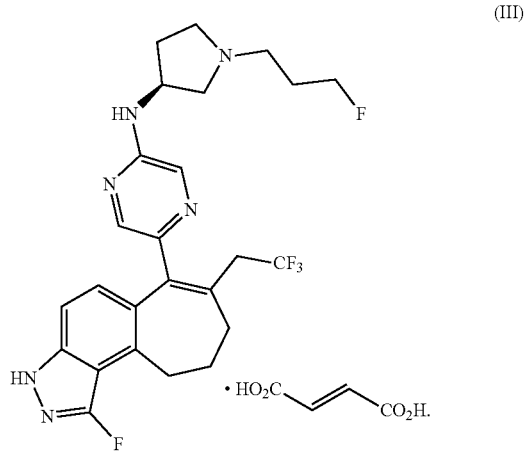 [SMILES: FCCCN1CC[C@H](Nc2cnc(C3=C(CC(F)(F)F)CCCc4c3ccc3[nH]nc(F)c43)cn2)C1 ; O=C(O)/C=C/C(=O)O]

(III)

2. A crystal form A of the compound of formula (III) according to claim 1,

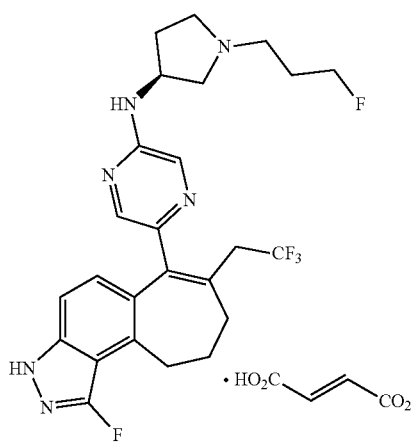

(III)

wherein the crystal form A has an X-ray powder diffraction pattern having characteristic diffraction peaks at the following 2θ angles: 12.30±0.20°, 15.64±0.20°, 17.00±0.20°, 18.26±0.20°, 20.92±0.20°, 22.08±0.20°, 22.62±0.20°, and 24.70±0.20°.

3. The crystal form A of the compound of formula (III) according to claim 2, wherein the X-ray powder diffraction pattern thereof has diffraction peaks at the following 2θ angles: 5.18±0.20°, 5.92±0.20°, 8.12±0.20°, 12.30±0.20°, 15.64±0.20°, 17.00±0.20°, 18.26±0.20°, 20.92±0.20°, 22.08±0.20°, and 24.70±0.20°.

4. The crystal form A of the compound of formula (III) according to claim 3, wherein the X-ray powder diffraction pattern thereof has diffraction peaks at the following 2θ angles: 5.18±0.20°, 5.92±0.20°, 8.12±0.20°, 12.30±0.20°, 15.64±0.20°, 17.00±0.20°, 18.26±0.20°, 19.54±0.20°, 20.92±0.20°, 22.08±0.20°, 22.62±0.20°, and 24.70±0.20°.

5. The crystal form A of the compound of formula (III) according to claim 3, wherein the X-ray powder diffraction pattern thereof has diffraction peaks at the following 2θ angles: 5.18±0.20°, 5.92±0.20°, 8.12±0.20°, 12.30±0.20°, 15.64±0.20°, 17.00±0.20°, 18.26±0.20°, 19.54±0.20°, 20.92±0.20°, 22.08±0.20°, 24.70±0.20°, and 25.48±0.20°.

6. The crystal form A of the compound of formula (III) according to claim 3, wherein the X-ray powder diffraction pattern thereof has diffraction peaks at the following 2θ angles: 5.18±0.20°, 5.92±0.20°, 8.12±0.20°, 12.30±0.20°, 15.64±0.20°, 17.00±0.20°, 18.26±0.20°, 19.54±0.20°, 20.92±0.20°, 22.08±0.20°, 22.62±0.20°, 24.70±0.20°, and 25.48±0.20°.

7. The crystal form A of the compound of formula (III) according to claim 2, wherein the X-ray powder diffraction pattern thereof has diffraction peaks at the following 2θ angles: 5.18±0.20°, 5.92±0.20°, 8.12±0.20°, 12.30±0.20°, 15.64±0.20°, 16.42±0.20°, 17.00±0.20°, 17.66±0.20°, 18.26±0.20°, 19.54±0.20°, 20.06±0.20°, 20.92±0.20°, 22.08±0.20°, 22.62±0.20°, 23.32±0.20°, 23.86±0.20°, 24.70±0.20°, 25.48±0.20°, 26.68±0.20°, 28.50±0.20°, 29.54±0.20°, 31.58±0.20°, and 33.20±0.20°.

8. The crystal form A of the compound of formula (III) according to claim 2, wherein the X-ray powder diffraction pattern thereof has diffraction peaks at the following 2θ angles: 5.181°, 5.920°, 8.119°, 12.299°, 15.638°, 16.418°, 17.002°, 17.660°, 18.261°, 19.539°, 20.061°, 20.919°, 22.080°, 22.621°, 23.320°, 23.861°, 24.700°, 25.483°, 26.681°, 28.498°, 29.542°, 31.578°, and 33.198°.

9. The crystal form A of the compound of formula (III) according to claim 2, wherein the crystal form A has a thermogravimetric analysis curve with a weight loss of 0.198% at 150.000±3° C. and a weight loss of 10.880% at 240.000±3° C.

10. The crystal form A of the compound of formula (III) according to claim 2, wherein the crystal form A has a differential scanning calorimetry curve comprising endothermic peaks with onsets at 175.87±5° C., 214.68±5° C., and 292.11±5° C.

11. A crystal form B of a compound of formula (II),

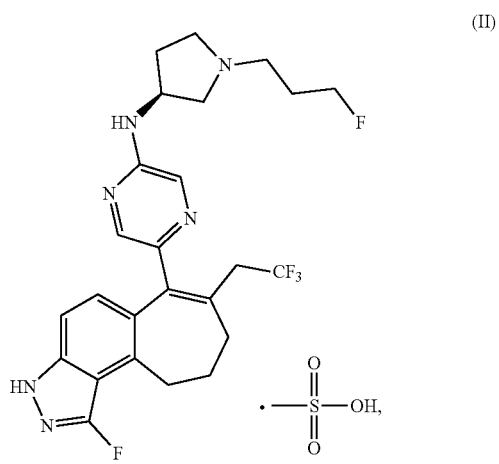

(II)

wherein the crystal form B has an X-ray powder diffraction pattern having characteristic diffraction peaks at the following 2θ angles: 6.50±0.20°, 14.24±0.20°, 15.80±0.20°, 18.18±0.20°, 22.18±0.20°, 23.78±0.20°, and 25.30±0.20°.

12. The crystal form B of the compound of formula (II) according to claim 11, wherein the X-ray powder diffraction pattern thereof has diffraction peaks at the following 2θ angles: 6.50±0.20°, 7.86±0.20°, 14.24±0.20°, 15.80±0.20°, 16.92±0.20°, 18.18±0.20°, 19.66±0.20°, 20.76±0.20°, 22.18±0.20°, 23.78±0.20°, 25.30±0.20°, and 26.12±0.20°.

13. The crystal form B of the compound of formula (II) according to claim 12, wherein the X-ray powder diffraction pattern thereof has diffraction peaks at the following 2θ angles: 6.499°, 7.860°, 9.739°, 10.257°, 11.862°, 12.255°, 13.021°, 14.240°, 15.417°, 15.797°, 16.541°, 16.920°, 17.558°, 18.182°, 18.439°, 18.702°, 19.660°, 20.381°, 20.761°, 21.494°, 21.647°, 22.180°, 23.781°, 24.099°, 24.498°, 25.304°, 26.118°, 26.821°, 27.239°, 28.579°, 28.924°, 29.302°, 29.881°, 30.278°, 30.681°, 30.938°, 31.764°, 32.978°, 34.260°, 35.101°, 35.419°, 35.761°, 36.597°, 37.083°, 37.540°, and 38.423°.

14. The crystal form B of the compound of formula (II) according to claim 13, wherein the crystal form B has a thermogravimetric analysis curve with a weight loss of 0.085% at 200.000±3° C.

15. A crystal form C of a compound of formula (I)

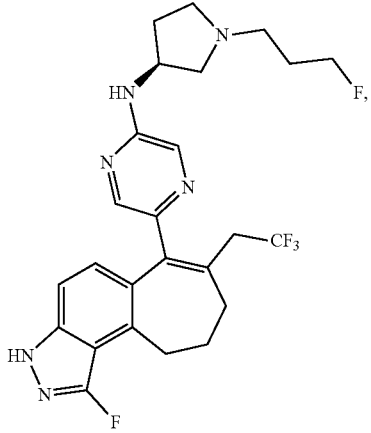

wherein the crystal form C has an X-ray powder diffraction pattern having characteristic diffraction peaks at the following 2θ angles: 4.90±0.20°, 9.82±0.20°, 15.82±0.20°, 17.48±0.20°, 18.64±0.20°, 22.26±0.20°, 23.74±0.20°, and 29.36±0.20°.

16. The crystal form C of the compound of formula (I) according to claim 15, wherein the X-ray powder diffraction pattern thereof has diffraction peaks at the following 2θ angles: 3.30±0.20°, 4.90±0.20°, 9.82±0.20°, 11.06±0.20°, 14.20±0.20°, 15.82±0.20°, 17.48±0.20°, 18.64±0.20°, 22.26±0.20°, 23.74±0.20°, 24.46±0.20°, and 29.36±0.20°.

17. The crystal form C of the compound of formula (I) according to claim 16, wherein the X-ray powder diffraction pattern thereof has diffraction peaks at the following 2θ angles: 3.301°, 4.901°, 7.898°, 9.319°, 9.819°, 11.061°, 14.200°, 14.721°, 15.197°, 15.821°, 16.457°, 17.481°, 18.101°, 18.642°, 19.762°, 20.961°, 21.382°, 22.259°, 23.740°, 24.461°, 25.761°, 26.295°, 26.943°, 27.518°, 29.358°, 30.075°, 31.317°, 31.916°, 34.598°, and 37.661°.

* * * * *